(12) United States Patent
Capet et al.

(10) Patent No.: US 7,432,269 B2
(45) Date of Patent: Oct. 7, 2008

(54) ARYLPIPERASZINE DERIVATIVES, TO THE PROCESS FOR THE PRODUCTION THEREOF AND TO THE USE THEREOF AS THERAPEUTIC AGENTS

(75) Inventors: Marc Capet, Melesse (FR); Denis Danvy, Yvetot (FR); Nicolas Levoin, Mordelles (FR); Marcel Morvan, Pace (FR); Isabelle Berrebi-Bertrand, Pace (FR); Thierry Calmels, Melesse (FR); Philippe Robert, Pace (FR); Jean-Charles Schwartz, Paris (FR); Jeanne-Marie Lecomte, Paris (FR)

(73) Assignee: Bioprojet, Paris (FR)

( * ) Notice: Subject to any disclaimer, the term of this patent is extended or adjusted under 35 U.S.C. 154(b) by 29 days.

(21) Appl. No.: 11/252,870

(22) Filed: Oct. 19, 2005

(65) Prior Publication Data
US 2006/0089364 A1   Apr. 27, 2006

(30) Foreign Application Priority Data
Oct. 22, 2004   (FR) .................................. 04 11303

(51) Int. Cl.
A61K 31/497   (2006.01)
C07D 401/00   (2006.01)
C07D 413/00   (2006.01)
C07D 417/00   (2006.01)

(52) U.S. Cl. .......................... 514/253.01; 514/253.05; 514/253.06; 514/254.02; 544/360; 544/363; 544/369

(58) Field of Classification Search ...................... None
See application file for complete search history.

(56) References Cited

U.S. PATENT DOCUMENTS

| 6,224,849 | B1 | 5/2001 | Kennis et al. | |
| 2002/0052496 | A1 | 5/2002 | He et al. | |
| 2005/0043309 | A1* | 2/2005 | Clark et al. ................. | 514/249 |

FOREIGN PATENT DOCUMENTS

| DE | 2 258 561 | 6/1973 |
| WO | WO-98/56786 | 12/1998 |
| WO | WO-00/18767 | 4/2000 |
| ZA | 8504887 | * 2/1986 |

OTHER PUBLICATIONS

Yang et. al.; Raney Nickel; Apr. 15, 2006; Encyclopedia of Reagents for Organic Synthesis; p. 1-21.*
Roden et. eal.; Hydrazine; Apr. 15, 2001; Encyclopedia of Reagents for Organic Synthesis; p. 1-9.*
Vaquero et. al.; The Reactions of Benzomalononitriles with Hydrazine and Hydroxylamine. Synthesis of Pyrazoles, Isoxazoles, and Pyrazolo[1,5-a]-pyrimidine Derivatives.*
Vippagunta, et. al., Advanced Drug Delivery Reviews; 48, (2001) 3-26.*

* cited by examiner

Primary Examiner—James O. Wilson
Assistant Examiner—Jeffrey H Murray
(74) Attorney, Agent, or Firm—B. Aaron Schulman; Stites & Harbison PLLC

(57) ABSTRACT

The invention relates to compounds of the general formula (I):

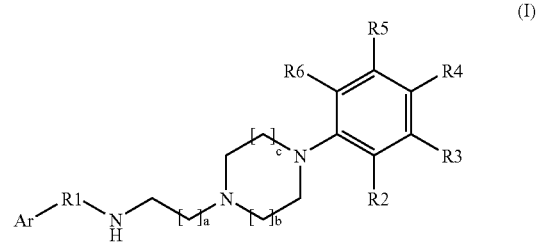

to the process for preparing them, and to the use thereof as a therapeutic agent having the property of being selective ligands for the dopamine D3 receptor. These selective D3 ligands are useful as medicines in neuropsychiatry, in particular in the treatment of psychotic or depressive states, or in the treatment of motor disorders, such as dyskinesia or essential tremor. They are furthermore useful in the treatment of dependency on nicotine, cocaine, alcohol, opioids and for facilitating withdrawal in drug-dependent individuals.

4 Claims, No Drawings

ARYLPIPERASZINE DERIVATIVES, TO THE PROCESS FOR THE PRODUCTION THEREOF AND TO THE USE THEREOF AS THERAPEUTIC AGENTS

TECHNICAL FIELD OF THE INVENTION

The present invention relates to novel arylpiperazine derivatives, to the process for the production thereof and to the use thereof as therapeutic agents.

More specifically, the compounds according to the present invention have the property of being selective ligands for the dopamine D3 receptor.

BACKGROUND OF THE INVENTION

Numerous arylpiperazine derivatives are already known as antagonists of dopamine's type D2 receptors, some of these derivatives having neuroleptic properties, or alternatively as serotonin or noradrenaline antagonists.

Patent DE 2 143 730 describes arylpiperazine derivatives having analgesic and antihypertensive properties; however, these compounds have a heteroaryl ring which is optionally substituted by various non-aromatic groups.

Patent applications WO 99/21848, WO 97/43271, WO 00/18767, WO 98/56786 and DE 2258561 also describe compounds of a closely related structure.

It has now completely unexpectedly been found that the compounds according to the invention, which constitute a new series of arylpiperazine derivatives, exhibit a strong affinity for the dopamine D3 receptor.

These selective D3 ligands are useful as medicines in neuropsychiatry, in particular in the treatment of psychotic or depressive states, or in the treatment of motor disorders, such as dyskinesia or essential tremor. They are furthermore useful in the treatment of dependency on nicotine, cocaine, alcohol, opioids and for facilitating withdrawal in drug-dependent individuals.

SUMMARY OF THE INVENTION

The present invention accordingly relates to the compounds of the formula (I):

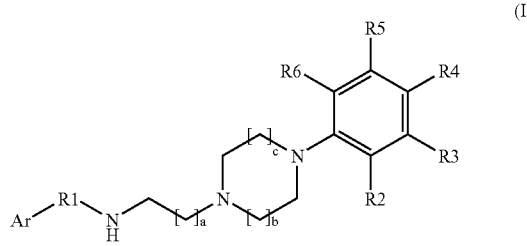

in which:
R1 represents a heteroaryl with five or six chain links, optionally containing one or more heteroatoms, selected from among 2-pyridyl, 2-pyrimidinyl, 2-pyridazinyl, 2-pyrazinyl, 2-imidazolyl, 2-oxazolyl, 2-thiazolyl, 3-isoxazolyl, 3-isothiazolyl, 1,2,4-triazol-2-yl, 1,3,4-oxadiazol-2-yl, 1,3,4-thiadiazol-2-yl, optionally substituted by one or more identical or different groups selected from among a halogen atom or a hydroxy, alkyl, monofluoroalkyl, polyfluoroalkyl, alkoxy, polyfluoroalkoxy, alkylsulfanyl, polyfluoroalkylsulfanyl group;

Ar is an aryl or heteroaryl, optionally fused with R1 and optionally substituted by one or more identical or different substituents selected from among a halogen atom or a hydroxy, alkyl, monofluoroalkyl, polyfluoroalkyl, alkoxy, polyfluoroalkoxy, alkylsulfanyl, polyfluoroalkylsulfanyl, cyano, carbamoyl, dialkylcarbamoyl, alkyl-C(=O)—, alkyl-O—C(=O)—, HO—C(=O)—, (HO)alkyl group, or Ar is fused with a saturated, unsaturated or aromatic hydrocarbon cycle or heterocycle;

a=2, 3 or 4;

b and c, identical or different, represent 1 or 2;

R2, R3, R4, R5 and R6 each independently represent a hydrogen or halogen atom or a hydroxy, alkyl, monofluoroalkyl, polyfluoroalkyl, alkoxy, polyfluoroalkoxy, alkylsulfanyl, polyfluoroalkylsulfanyl, cyano, —NRR', —COOR, —COR, —CONRR' group or alternatively two adjacent R2, R3, R4, R5 and R6 are joined to one another to form a hydrocarbon cycle or a saturated or unsaturated heterocycle, fused to the phenyl nucleus to which they are attached;

where R, R', identical or different, independently represent a hydrogen atom, or an alkyl group;

together with the stereoisomers or mixtures thereof, the tautomeric forms thereof, the hydrates, solvates thereof, the pharmaceutically acceptable salts and esters thereof.

BEST MODE OF THE INVENTION

Preferably, the present invention relates to compounds of the formula (I) in which:
R1 represents a heteroaryl with five or six chain links, optionally containing one or more heteroatoms, selected from among 2-pyridyl, 2-pyrimidinyl, 2-pyridazinyl, 2-pyrazinyl, 2-imidazolyl, 2-oxazolyl, 2-thiazolyl, 3-isoxazolyl, 3-isothiazolyl, 1,2,4-triazol-2-yl, 1,3,4-oxadiazol-2-yl, 1,3,4-thiadiazol-2-yl, optionally substituted by one or more identical or different groups selected from among a halogen atom or a hydroxy, alkyl, monofluoroalkyl, polyfluoroalkyl, alkoxy, polyfluoroalkoxy, alkylsulfanyl, polyfluoroalkylsulfanyl group;

Ar is an aryl or heteroaryl, not fused to R1, optionally substituted by one or more identical or different substituents selected from among a halogen atom or a hydroxy, alkyl, monofluoroalkyl, polyfluoroalkyl, alkoxy, polyfluoroalkoxy, alkylsulfanyl, polyfluoroalkylsulfanyl, cyano, carbamoyl, dialkylcarbamoyl, alkyl-C(=O)—, alkyl-O—C(=O)—, HO—C(=O)—, (HO)alkyl group, or Ar is fused with a saturated, unsaturated or aromatic hydrocarbon cycle or heterocycle;

a=2, 3 or 4;

b and c, identical or different, represent 1 or 2;

R2, R3, R4, R5 and R6 each independently represent a hydrogen or halogen atom or a hydroxy, alkyl, monofluoroalkyl, polyfluoroalkyl, alkoxy, polyfluoroalkoxy, alkylsulfanyl, polyfluoroalkylsulfanyl, cyano, —NRR', —COOR, —COR, —CONRR' group or alternatively two adjacent R2, R3, R4, R5 and R6 are joined to one another to form a hydrocarbon cycle or a saturated or unsaturated heterocycle, fused to the phenyl nucleus to which they are attached;

where R, R', identical or different, independently represent a hydrogen atom, or an alkyl group;

together with the stereoisomers or mixtures thereof, the tautomeric forms thereof, the hydrates, solvates thereof, the pharmaceutically acceptable salts and esters thereof.

Preferably, R1 represents 2-pyridyl.

Preferably, Ar is an aryl, more preferably phenyl, optionally substituted by one or more identical or different substituents selected from among a halogen atom or an alkyl group.

Preferably, -a=3.

Preferably, b and c represent 1.

Preferably, R2, R3, R4, R5 and R6 each independently represent a hydrogen or halogen atom or a polyfluoroalkyl group, such as a perfluoroalkyl group, such as trifluoromethyl.

The compounds of the formula (I) may in particular be selected from among:

2-{4-[4-(2-fluorophenyl)piperazin-1-yl]butyl}amino-5-phenylpyridine

2-{4-[4-(2-fluorophenyl)piperazin-1-yl]butyl}amino-4-phenylpyridine

2-{4-[4-(3-trifluoromethylphenyl)piperazin-1-yl]butyl}amino-4-phenylpyridine

2-{4-[4-(3-trifluoromethylphenyl)piperazin-1-yl]butyl}amino-4-phenylpyridine dihydrochloride 2-{4-[4-(3-trifluoromethylphenyl)piperazin-1-yl]butyl}amino-5-phenylpyridine 2-{4-[4-(2,3-dichlorophenyl)piperazin-1-yl]butyl}amino-4-phenylpyridine 2-{4-[4-(2,3-dichlorophenyl)piperazin-1-yl]butyl}amino-5-phenylpyridine 2-{4-[4-(2,3-dichlorophenyl)piperazin-1-yl]butyl}amino-5-(2-methylphenyl)-pyridine 2-{4-[4-(3-trifluoromethylphenyl)piperazin-1-yl]butyl}amino-5-(2-methylphenyl)-pyridine 2-{4-[4-(3-trifluoromethylphenyl)piperazin-1-yl]butyl}amino-5-(4-fluorophenyl)-pyridine 2-{4-[4-(3-trifluoromethylphenyl)piperazin-1-yl]butyl}amino-4-(2-methylphenyl)-pyridine 2-{4-[4-(2,3-dichloromethylphenyl)piperazin-1-yl]butyl}amino-4-(2-methylphenyl)pyridine 2-{4-[4-(2-cyano-3-trifluoromethylphenyl)piperazin-1-yl]butyl}amino-4-phenylpyridine 2-{4-[4-(3-chlorophenyl)piperazin-1-yl]butyl}amino-4-phenylpyridine 2-{4-[4-(5,6,7,8-tetrahydro-1-naphthyl)piperazin-1-yl]butyl}amino-4-phenylpyridine dihydrochloride 2-{4-[4-(2-cyano-3-isopropoxyphenyl)piperazin-1-yl]butyl}amino-4-phenylpyridine 2-{4-[4-(3-trifluoromethylphenyl)piperazin-1-yl]butyl}amino-4-(4-fluorophenyl)-pyridine 2-{4-[4-(3-trifluoromethylphenyl)piperazin-1-yl]butyl}amino-4-(4-chlororophenyl)pyridine 2-{4-[4-(3-trifluoromethylphenyl)piperazin-1-yl]butyl}amino-4-(3-fluorophenyl)-pyridine 2-{4-[4-(3-trifluoromethylphenyl)piperazin-1-yl]butyl}amino-4-(4-methoxyphenyl)pyridine 2-{4-[4-(3-trifluoromethylphenyl)piperazin-1-yl]butyl}amino-4-(3-thienyl)-pyridine 2-{4-[4-(3-trifluoromethylphenyl)piperazin-1-yl]butyl}amino-4-(2-furyl)pyridine 2-{4-[4-(3-trifluoromethylphenyl)piperazin-1-yl]butyl}amino-4-(2-thienyl)-pyridine 2-{4-[4-(3-trifluoromethylphenyl)piperazin-1-yl]butyl}amino-4-(2-fluorophenyl)-pyridine 2-{4-[4-(3-trifluoromethylphenyl)piperazin-1-yl]butyl}amino-[4,4']bipyridine 2-{4-[4-(3-trifluoromethylphenyl)piperazin-1-yl]butyl}amino-4-(3-methylphenyl)-pyridine 2-{4-[4-(3-trifluoromethylphenyl)piperazin-1-yl]butyl}amino-4-(3-methoxyphenyl)pyridine 2-{4-[4-(3-trifluoromethylphenyl)piperazin-1-yl]butyl}amino[4,3']bipyridine 2-{4-[4-(3-trifluoromethylphenyl)piperazin-1-yl]butyl}amino-4-(4-trifluoromethoxyphenyl)pyridine 2-{4-[4-(3-trifluoromethylphenyl)piperazin-1-yl]butyl}amino-4-(4-acetylphenyl)-pyridine 2-{4-[4-(3-trifluoromethylphenyl)piperazin-1-yl]butyl}amino-4-(3-acetyl phenyl)-pyridine 2-{4-[4-(3-trifluoromethylphenyl)piperazin-1-yl]butyl}amino-4-(4-hydroxymethylphenyl)pyridine 2-{4-[4-(3-trifluoromethylphenyl)piperazin-1-yl]butyl}amino-4-(benzo[1,3]dioxol-5-yl)pyridine 2-{4-[4-(3-trifluoromethylphenyl)piperazin-1-yl]butyl}amino-4-(4-ethoxycarbonylphenyl)pyridine 2-{4-[4-(3-trifluoromethylphenyl)piperazin-1-yl]butyl}amino-4-(4-(1-hydroxyethyl)phenyl)pyridine 2-{4-[4-(3-trifluoromethylphenyl)piperazin-1-yl]butyl}amino-4-(4-(1-hydroxy-1-ethylethyl)phenyl)pyridine 2-{4-[4-(3-trifluoromethylphenyl)piperazin-1-yl]butyl}amino-4-(3-(1-hydroxy-1-methylethyl)phenyl)pyridine 2-{4-[4-(3-trifluoromethylphenyl)piperazin-1-yl]butyl}amino-4-(4-carboxyphenyl)pyridine sodium salt 2-{4-[4-(3-trifluoromethylphenyl)piperazin-1-yl]butyl}amino-4-phenylthiazole 2-{4-[4-(3-trifluoromethylphenyl)piperazin-1-yl]butyl}amino-5-phenyloxazole 2-{4-[4-(3-trifluoromethylphenyl)piperazin-1-yl]butyl}aminoquinoline hydrochloride 1-{4-[4-(3-trifluoromethylphenyl)piperazin-1-yl]butyl}aminoisoquinoline hydrochloride 2-{4-[4-(2,3-dichlorophenyl)piperazin-1-yl]butyl}aminoquinoline hydrochloride 1-{4-[4-(2,3-dichlorophenyl)piperazin-1-yl]butyl}aminoisoquinoline hydrochloride together with the stereoisomers or mixtures thereof, the tautomeric forms thereof, the hydrates, solvates thereof, the pharmaceutically acceptable salts, free forms and esters thereof.

More preferably, the compounds of the formula (I) may be selected from among:

2-{4-[4-(3-trifluoromethylphenyl)piperazin-1-yl]butyl}amino-4-phenylpyridine

2-{4-[4-(3-trifluoromethylphenyl)piperazin-1-yl]butyl}amino-4-phenylpyridine dihydrochloride 2-{4-[4-(2,3-dichlorophenyl)piperazin-1-yl]butyl}amino-4-phenylpyridine, together with the stereoisomers or mixtures thereof, the tautomeric forms thereof, the hydrates, solvates thereof, the pharmaceutically acceptable salts, free forms and esters thereof.

According to the present invention, alkyl residues represent straight-chain or branched, saturated hydrocarbon residues with 1 to 20 carbon atoms, preferably from 1 to 5 carbon atoms.

When linear, methyl, ethyl, propyl, butyl, pentyl, hexyl, octyl, nonyl, decyl, dodecyl, hexadecyl, and octadecyl residues may in particular be mentioned.

When branched or substituted by one or more alkyl residues, isopropyl, tert-butyl, 2-ethylhexyl, 2-methylbutyl, 2-methylpentyl, 1-methylpentyl and 3-methylheptyl residues may in particular be mentioned.

Alkoxy residues according to the present invention are residues of the formula —O-alkyl, the alkyl being as defined previously.

Halogen atoms which may more particularly be mentioned are fluorine, chlorine, bromine and iodine atoms, preferably fluorine.

Alkenyl residues represent straight-chain or linear hydrocarbon residues and comprise one or more ethylenic unsaturations. Alkenyl residues which may in particular be mentioned are allyl or vinyl residues.

Alkynyl residues represent straight-chain or linear hydrocarbon residues and comprise one or more acetylenic unsaturations. Acetylene may in particular be mentioned among alkynyl residues.

The cycloalkyl residue is a non-aromatic, saturated or partially unsaturated mono-, bi- or tricyclic hydrocarbon residue, with 3 to 10 carbon atoms, such as in particular cyclopropyl, cyclopentyl, cyclohexyl or adamantyl, together with corresponding cycles containing one or more unsaturations.

Aryl denotes a mono- or bicyclic aromatic hydrocarbon system with 6 to 10 carbon atoms.

Aryl residues which may in particular be mentioned are the phenyl or naphthyl residue, more particularly substituted by at least one halogen atom.

-Alkylaryl residues which may in particular be mentioned are the benzyl or phenethyl residue.

Heteroaryl residues denote mono- or bicyclic aromatic systems with 5 to 10 carbon atoms comprising one or more heteroatoms selected from among nitrogen, oxygen or sulfur. Heteroaryl residues which may be mentioned are pyrazinyl, thienyl, oxazolyl, furazanyl, pyrrolyl, 1,2,4-thiadiazolyl, naphthyridinyl, pyridazinyl, quinoxalinyl, phthalazinyl, imidazo[1,2-a]pyridine, imidazo[2,1-b]thiazolyl, cinnolinyl, triazinyl, benzofurazanyl, azaindolyl, benzimidazolyl, benzothienyl, thienopyridyl, thienopyrimidinyl, pyrrolopyridyl, imidazopyridyl, benzoazaindole, 1,2,4-triazinyl, benzothiazolyl, furanyl, imidazolyl, indolyl, triazolyl, tetrazolyl, indolizinyl, isoxazolyl, isoquinolinyl, isothiazolyl, oxadiazolyl, pyrazinyl, pyridazinyl, pyrazolyl, pyridyl, pyrimidinyl, purinyl, quinazolinyl, quinolinyl, isoquinolyl, 1,3,4-thiadiazolyl, thiazolyl, triazinyl, isothiazolyl, carbazolyl, together with the corresponding groups arising from the fusion thereof or from fusion with the phenyl nucleus.

The phrase "pharmaceutically acceptable salts" refers to the relatively non-toxic inorganic and organic acid addition salts, and base addition salts, of the compounds of the present invention. These salts may be prepared in situ during final isolation and purification of the compounds. In particular, the acid addition salts may be prepared by separately reacting the purified compound in its clean form with an organic or inorganic acid and isolating the resultant salt. Examples of acid addition salts include hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptanate, lactobionate, sulfamates, malonates, salicylates, propionates, methylenebis-beta-hydroxynaphthoates, gentisic acid, isethionates, di-p-toluoyltartrates, methanesulfonates, ethanesulfonates, benzenesulfonates, p-toluenesulfonates, cyclohexyl sulfamates and quinate lauryl sulfonate, and the like. (See for example S. M. Berge et al. "Pharmaceutical Salts" *J. Pharm. Sci*, 66: p. 1-19 (1977) which is incorporated herein by reference). The acid addition salts may also be prepared by separately reacting the purified compound in its acid form with an organic or inorganic base and isolating the resultant salt. Acid addition salts include amine and metal salts. Suitable metal salts comprise the salts of sodium, potassium, calcium, barium, zinc, magnesium and aluminium. Sodium and potassium salts are preferred. Suitable inorganic base addition salts are prepared from metallic bases which comprise sodium hydride, sodium hydroxide, potassium hydroxide, calcium hydroxide, aluminium hydroxide, lithium hydroxide, magnesium hydroxide, zinc hydroxide. Suitable amine base addition salts are prepared from amines which have sufficient alkalinity to form a stable salt, and preferably comprise the amines which are frequently used in medicinal chemistry due to their low toxicity and their acceptability for medical use: ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, for example lysine and arginine, and dicyclohexylamine, and the like.

The invention also relates to the stereoisomers or mixtures thereof, the tautomeric forms, the pharmaceutically acceptable hydrates, solvates, salts and esters of compounds of the formula (I).

The compounds of the invention of the formula (I) as defined above having a sufficiently acidic function or a sufficiently basic function or both, may include the corresponding pharmaceutically acceptable salts of an organic or inorganic acid or of an organic or inorganic base.

The compounds of general formula (I) may be prepared by applying or adapting any method known per se and/or within the capability of the person skilled in the art, in particular those described by Larock in *Comprehensive Organic Transformations*, VCH Pub., 1989, or by applying or adapting the processes described in the following Examples.

According to another object, the present invention accordingly also relates to the process for preparing the previously described compounds of the formula (I) comprising the step of coupling compounds of the formulae (II) and (III) in accordance with the following scheme:

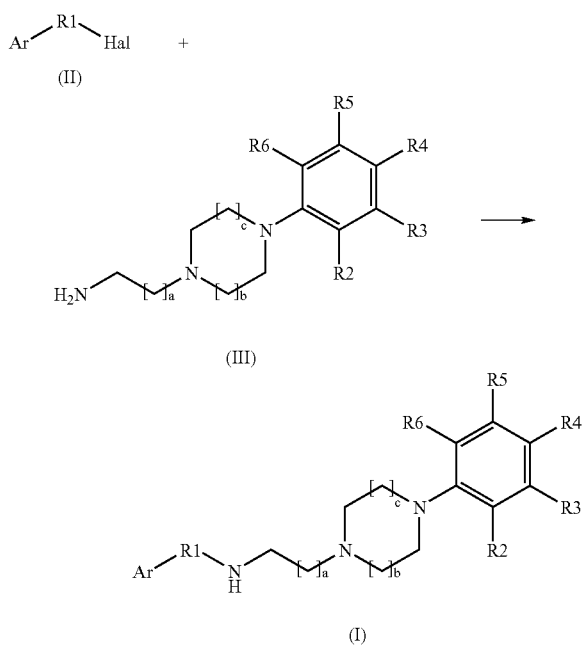

where, in the formulae (II) and (III), Ar, R1, R2, R3, R4, R5, R6, a, b and c have the same meaning as in the formula (I) and Hal represents a halogen atom, preferably chlorine.

In general, the substitution is performed by heating to 300-350° C. or by heating in a microwave oven. This reaction may likewise be catalysed by organic compounds (phenol derivatives, 4-dimethylaminopyridine, trifluoroethanol) or inorganic compounds (alkali or alkaline earth metal fluorides, transition metals such as palladium or nickel).

Derivatives of the formula (II) in which R1, of the formula

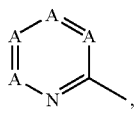

and A independently represents a carbon or nitrogen atom, represents an azine or diazine structural unit and for which Ar has the same meaning as in the formula (I), may be prepared from the N-oxides thereof of the formula (IV) in which Ar has the same meaning as in the formula (I) and each of the instances of A independently represents a carbon or nitrogen atom, in accordance with the following scheme:

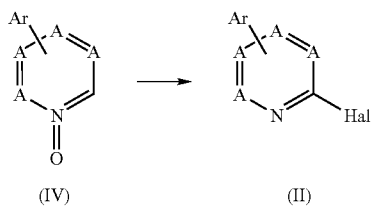

This reaction may be performed by reaction on a halogenating, in particular chlorinating, agent, such as phosphorus oxychloride, phosphorus trichloride, phosphorus pentachloride or sulfonyl chloride, optionally in the presence of an inorganic chloride (sodium chloride) in an organic solvent such as toluene or chloroform or without solvent at a temperature of between 0° C. and the boiling point of the reaction medium.

The azine or diazine N-oxides of the formula (IV) in which Ar has the same meaning as in the formula (I) and each of the instances of A independently represents a carbon or nitrogen atom, may be obtained by coupling between an arylboronic compound and a haloazine or halodiazine N-oxide (V) in which Ar has the same meaning as in the formula (I) and each of the instances of A independently represents a carbon or nitrogen atom:

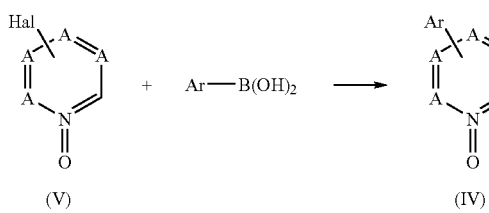

This reaction may be performed in the presence of a catalytic quantity of a transition metal such as palladium.

The derivatives of the formula (I) in which R1 represents an azine or diazine structural unit may also be prepared by reduction of their N-oxides of the formula (VI) in which Ar, R2, R3, R4, R5, R6, a, b and c have the same meaning as in the formula (I) and each of the instances of A independently represents a carbon or nitrogen atom.

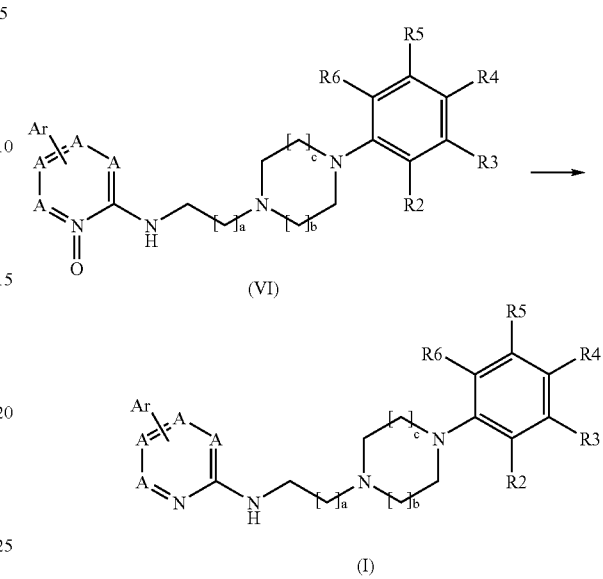

Reduction of the N-oxide function may be performed with the assistance of phosphorus trichloride in chloroform at ambient temperature, by phosphines such as triphenylphosphine in toluene, by hydrogenation with the assistance of molecular hydrogen or by transfer (formic acid, formate, cyclohexene, cyclohexadiene) in the presence of a transition metal (palladium on carbon) in an organic solvent such as toluene or an alcohol.

The N-oxides of the formula (VI), in which Ar, R2, R3, R4, R5, R6, a, b and c have the same meaning as in the formula (I) and each of the instances of A independently represents a carbon or nitrogen atom, may be prepared from haloazine N-oxides or halodiazine N-oxides of the formula (VII), in particular chloroazine N-oxides or chlorodiazine N-oxides, in which Ar has the same meaning as in the formula (I) and each of the instances of A independently represents a carbon or nitrogen atom and amines of the formula (III) in which R2, R3, R4, R5, R6, a, b and c have the same meaning as in the formula (I).

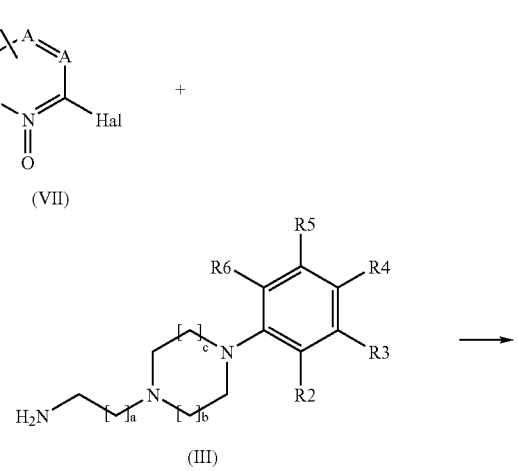

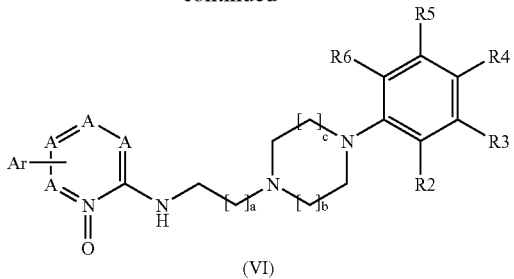

(VI)

Substitution of the haloazine N-oxide or halodiazine N-oxide derivatives of the formula (VII) may be performed in the presence of a base, such as sodium hydrogencarbonate for example, in tert.-amyl-alcohol at reflux overnight. This reaction may also be performed by heating to 300-350° C. or by heating in a microwave oven. This reaction may also be catalysed by organic compounds (phenol derivatives, 4-dimethylaminopyridine, trifluoroethanol) or inorganic compounds (alkali or alkaline earth metal fluorides, transition metals such as palladium or nickel).

The haloazine N-oxides or halodiazine N-oxides of the formula (VII), in which Ar has the same meaning as in the formula (I) and each of the instances of A independently represents a carbon or nitrogen atom, may be obtained by oxidation of the haloheterocycles of the formula (II) in which R1 represents an azine or diazine structural unit and for which Ar has the same meaning as in the formula (I) and each of the instances of A independently represents a carbon or nitrogen atom

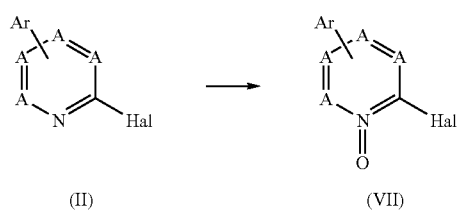

This oxidation may be performed by meta-chloroperbenzoic acid in chloroform at ambient temperature or with heat. It may also be performed by other oxidising agents such as hydrogen peroxide in the presence of acetic acid, formic acid, trifluoroacetic acid, acetic anhydride or trifluoroacetic anhydride; by the urea-hydrogen peroxide complex in dichloromethane or in formic acid for example and optionally in the presence of metal salts such as rhenium or tungsten oxides.

The chloroheterocycles of the formula (II), in which R1 represents an azine or diazine structural unit and for which Ar has the same meaning as in the formula (I) and each of the instances of A independently represents a carbon or nitrogen atom, may be prepared from N-oxides of the formula (IV) in which Ar has the same meaning as in the formula (I) and each of the instances of A independently represents a carbon or nitrogen atom as described above. They may also be prepared by coupling of an arylboronic compound with a haloazine or a halodiazine of the formula (VIII) in which Ar has the same meaning as in the formula (I), each of the instances of A independently represents a carbon or nitrogen atom and Hal' represents a bromine, an iodine or a pseudohalogen (paratoluenesulfonate, mesylate, triflate):

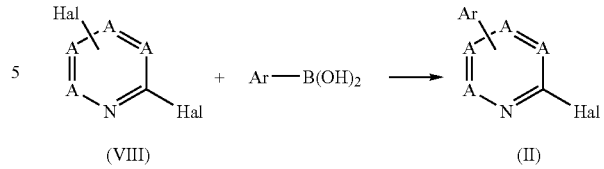

This reaction may be performed in the presence of a catalytic quantity of a transition metal such as palladium, in the presence of a base such as sodium carbonate in a solvent such as tetrahydrofuran or toluene at a temperature of between 0° C. and the boiling point of the reaction medium.

The amines of the formula (III), in which R2, R3, R4, R5, R6, a, b and c have the same meaning as in the formula (I), may be prepared by reduction of the nitriles of the formula (IX) in which R2, R3, R4, R5, R6, a, b and c have the same meaning as in the formula (I)

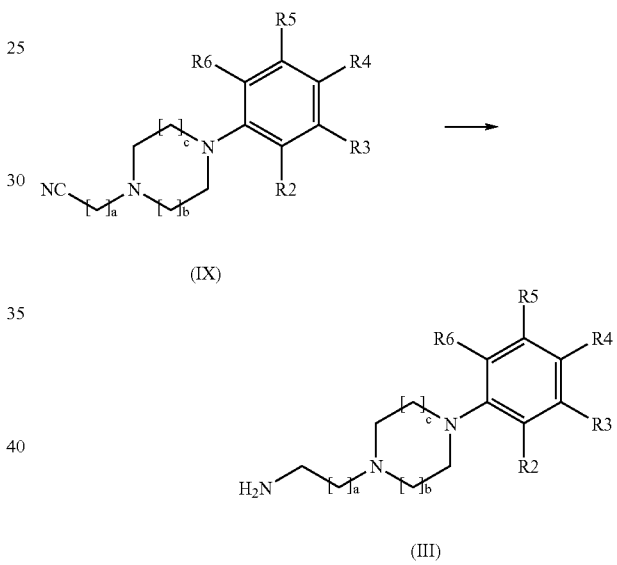

This reduction may be performed by molecular hydrogen in the presence of a transition metal (Raney nickel or palladium, for example) or by a hydride (double hydride of lithium and aluminium, for example).

The nitriles of the formula (IX) in which R2, R3, R4, R5, R6, a, b and c have the same meaning as in the formula (I) may be prepared from cyclic amines (X) in which R2, R3, R4, R5, R6, a, b and c have the same meaning as in the formula (I)

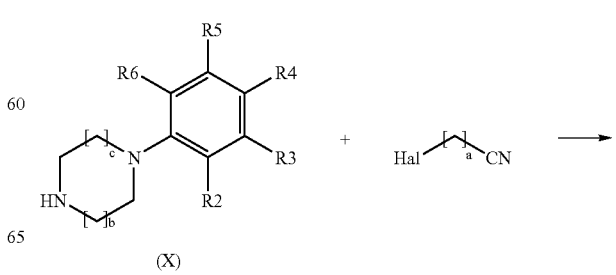

-continued

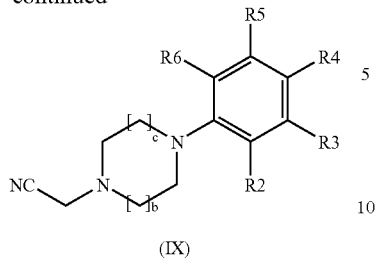

(IX)

where Hal represents a halogen atom, preferably bromine.

This reaction may be performed in the presence of an inorganic base (potassium carbonate) and in the presence or absence of a catalytic quantity of potassium iodide in acetonitrile at reflux.

The amines of the formula (III) in which R2, R3, R4, R5, R6, a, b and c have the same meaning as in the formula (I) may also be prepared from phthalimide derivatives (XI) in which R2, R3, R4, R5, R6, a, b and c have the same meaning as in the formula (I)

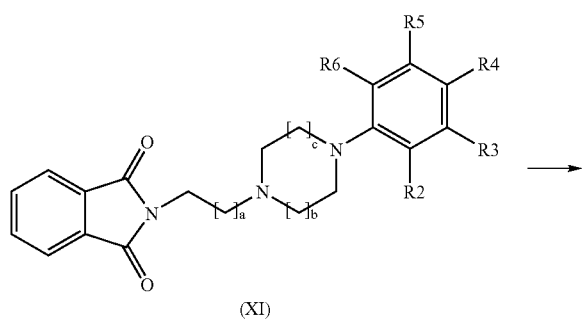

(XI)

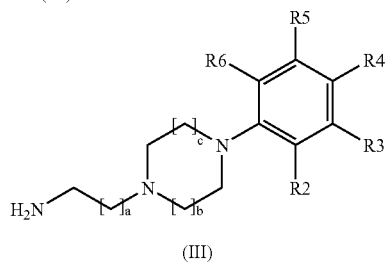

(III)

The phthalimide function may be deprotected with hydrazine monohydrate or methylhydrazine in an alcohol (methanol or ethanol) at a temperature of between 0° C. and 40° C. or alternatively by using the methods described or mentioned by J. O. Osby, M. G. Martin and B. Ganem, *Tetrahedron Lett.* 25(20) 2093-2096 (1984).

The phthalimide derivatives (XI) in which R2, R3, R4, R5, R6, a, b and c have the same meaning as in the formula (I) may be obtained from cyclic amine derivatives (X) in which R2, R3, R4, R5, R6, b and c have the same meaning as in the formula (I)

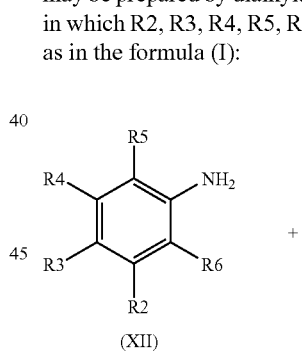

(X)

-continued

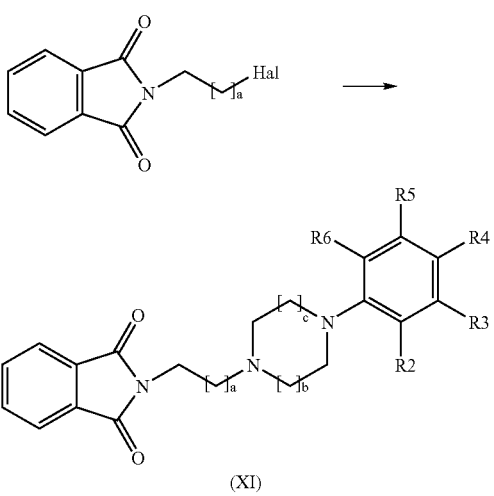

(XI)

where Hal represents a halogen atom, preferably bromine.

This alkylation may be performed with N-(ω-bromoalkyl) phthalimide in the presence of an inorganic base such as a carbonate or hydrogencarbonate, in the presence or absence of potassium iodide and in an organic solvent such as acetonitrile, N,N-dimethylformamide, dimethyl sulfoxide, N,N-dimethylacetamide or toluene at a temperature of between 20° C. and the boiling point of the reaction medium.

The cyclic amines of the formula (X) in which R2, R3, R4, R5, R6, b and c have the same meaning as in the formula (I) may be prepared by dialkylating anilines of the formula (XII) in which R2, R3, R4, R5, R6, b and c have the same meaning as in the formula (I):

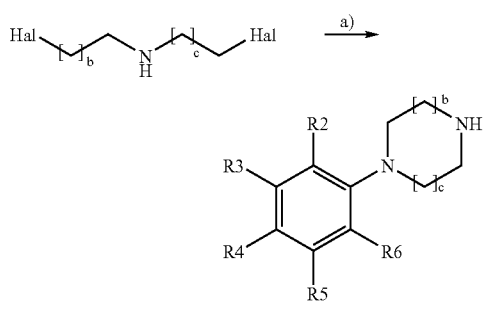

(XII)

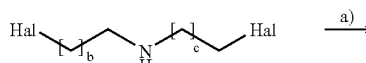

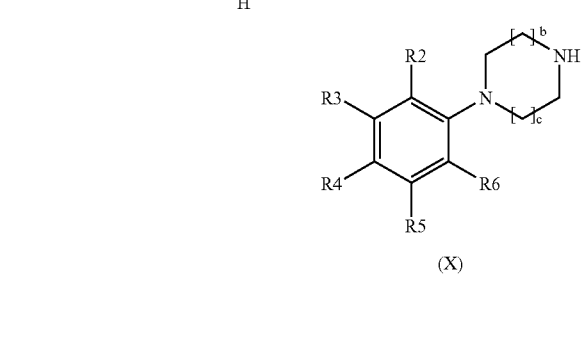

(X)

where Hal represents a halogen atom, preferably chlorine.

This reaction may be performed by heating in an aromatic solvent.

The cyclic amines of the formula (X) in which R2, R3, R4, R5, R6, b and c have the same meaning as in the formula (I) may also be prepared by substitution of haloaromatic compounds, preferably fluoroaromatic compounds of the formula (XIII) in which R2, R3, R4, R5 and R6 have the same meaning as in the formula (I) when the latter bears an electron-attracting group with a diamine of the formula (XIV) in which b and c have the same meaning as in the formula (I)

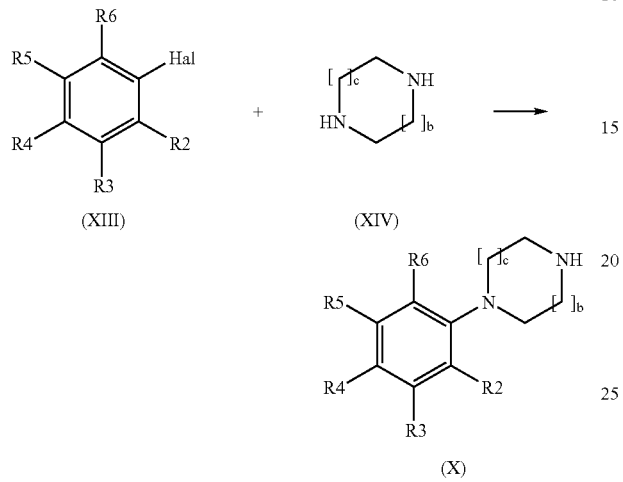

where Hal represents a halogen atom, preferably fluorine.

In general, this reaction is performed by heating in an organic solvent.

The cyclic amines of the formula (X) may also be prepared by substitution of a-haloaromatic compound, the halogen preferably being an iodine, a bromine or a chlorine or of a pseudohaloaromatic compound, the pseudohalogen being an arylsulfonate or an alkylsulfonate (paratoluenesulfonate, mesylate, triflate for example) of the formula (XIV).

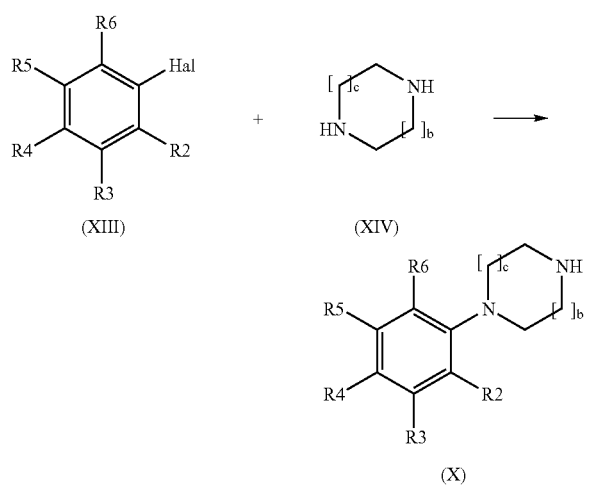

This reaction may optionally be catalysed by transition metals.

The derivatives of the formula (I) may also be prepared from amines of the formula (III) in which R2, R3, R4, R5, R6, a, b and c have the same meaning as in the formula (I) by construction of the heterocyclic moiety.

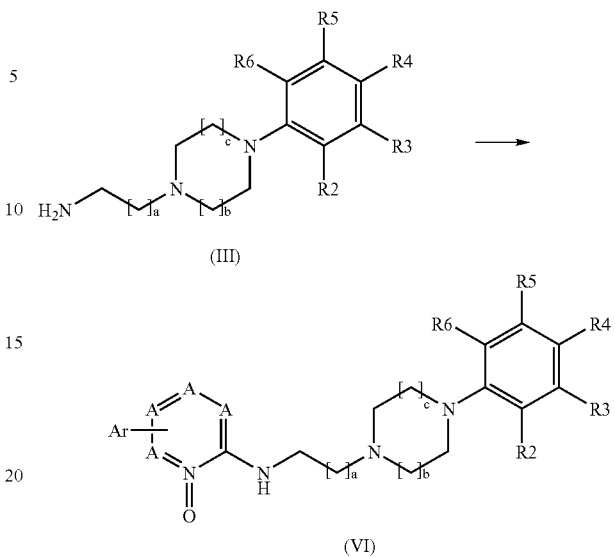

These heterocycle construction reactions may be performed in accordance with the methods described in *Bull. Soc. Chim. Fr.* 1163 (1956), *J. Med. Chem.* 1158 (1983), *J. Het. Chem.* 1377 (1979) *J. Prakt Chem.* 249 (1979) *Zh. Ob. Khim.* (Engl. Tr.) 2129 (1979), *J. Org. Chem.* 3736 (1974), *J. Het. Chem.* 873 (1976), *Carbohydrate Res.* 307 (1987), *J. Amer. Chem. Soc.* 2292 (1994), *Ber* 2110 (1966), *Rec. Trav. Chim. Netherlands* 463 (1942), *J. Org. Chem.* 2069 (1981), *Org. Lett.* 2091 (2002), *Phos. Sulf. Sil. Rel. El.* 81 (1991), *Bioorg. Med. Chem. Lett.* 3305 (2002), *Bioorg. Med. Chem. Lett.* 1345 (2003), *Bioorg. Med. Chem. Lett.* 3557 (2003), *Bull. Chem. Soc. Japan* 2450 (1984), *Heterocycles* 149 (1995), *J. Med. Chem.* 3977 (1994), *Helv. Chim. Acta* 1981 (1999), *Tetrahedron Lett.* 7825 (2003), *Pharm. Pharmacol. Commun.* 31 (2000), *J. Het. Chem.* 191 (2003), *J. Het. Chem.* 121 (2003), *Bioorg. Med. Chem.* 769 (2003), *Farmaco* 577 (2002).

Said process may optionally also comprise the step of isolating the product obtained.

In the reactions described here, it may be necessary to protect the reactive functional groups, for example the hydroxy, amino, imino, thio, carboxy groups, when they are desired in the final product, in order to avoid their unwanted participation in the reactions. Conventional protective groups may be used in accordance with standard practice, for examples see T. W. Greene and P. G. M. Wuts in *Protective Groups in Organic Chemistry*, John Wiley and Sons, 1991; J. F. W. McOmie in *Protective Groups in Organic Chemistry*, Plenum Press, 1973.

The compound prepared in this manner may be recovered from the reaction mixture by conventional means. For example, the compounds may be recovered by distilling the solvent from the reaction mixture or if necessary after distilling the solvent from the solution mixture, by pouring the residue into water followed by extraction with a water-immiscible organic solvent, and distilling the solvent from the extract. Furthermore, the product may, if so desired, be further purified by various methods, such as recrystallisation, reprecipitation or various chromatographic methods, in particular column chromatography or preparative thin layer chromatography.

It will be understood that the useful compounds according to the present invention may contain asymmetric centres. These asymmetric centres may independently be in R or S configuration. It will be apparent to the person skilled in the art that some of the useful compounds according to the invention may also exhibit geometric isomerism. It should be understood that the present invention comprises individual geometric isomers and stereoisomers and mixtures of the latter, including racemic mixtures, of compounds of the formula (I) above. This type of isomer may be separated from the mixtures thereof by applying or adapting known processes, for example chromatographic methods or recrystallisation methods, or they are prepared separately from the appropriate isomers of their intermediates.

For the purposes of the present document, it is understood that the tautomeric forms are included when a given group is mentioned, for example thio/mercapto or oxo/hydroxy.

The acid addition salts are formed with the useful compounds according to the invention in which a base function, such as an amino, alkylamino or dialkylamino group, is present. Pharmaceutically acceptable, i.e. non-toxic, acid addition salts are preferred. The selected salts are ideally chosen to be compatible with conventional pharmaceutical vehicles and to be capable of oral or parenteral administration. The acid addition salts of the useful compounds according to the present invention may be prepared by reaction of the free base with the appropriate acid, by applying or adapting known processes. For example, the acid addition salts of the useful compounds according to this invention may be prepared either by dissolving the free base in water or in an alcoholic aqueous solution or suitable solvents containing the appropriate acid and isolating the salt by evaporating the solution, or by reacting the free base and the acid in an organic solvent, in which case the salt separates out directly or may be obtained by concentrating the solution. Acids suitable for use in the preparation of these salts include hydrochloric acid, hydrobromic acid, phosphoric acid, sulfuric acid, various organic carboxylic and sulfonic acids, such as acetic acid, citric acid, propionic acid, succinic acid, benzoic acid, tartaric acid, fumaric acid, mandelic acid, ascorbic acid, malic acid, methanesulfonic acid, toluenesulfonic acid, fatty acids, adipate, alginate, ascorbate, aspartate, benzenesulfonate, benzoate, cyclopentylpropionate, digluconate, dodecylsulfate, bisulfate, butyrate, lactate, laurate, lauryl sulfate, malate, hydroiodide, 2-hydroxyethanesulfonate, glycerophosphate, picrate, pivalate, pamoate, pectinate, persulfate, 3-phenylpropionate, thiocyanate, 2-naphthalenesulfonate, undecanoate, nicotinate, hemisulfate, heptonate, hexanoate, camphorate, camphorsulfonate and others.

The acid addition salts of the useful compounds according to the present invention may be regenerated from salts by applying or adapting known processes. For example, useful parent compounds according to the invention may be regenerated from the acid addition salts thereof by treatment with an alkali, for example an aqueous solution of sodium bicarbonate or an aqueous ammonia solution.

The useful compounds according to the present invention may be regenerated from the base addition salts thereof by applying or adapting known processes. For example, the useful parent compounds according to the invention may be regenerated from the base addition salts thereof by treatment with an acid, for example hydrochloric acid.

The base addition salts may be formed when the useful compound according to the invention contains a carboxyl group, or a sufficiently acid bioisoster. The bases which may be used to prepare the base addition salts preferably comprise those which produce, when associated with a free acid, pharmaceutically acceptable salts, i.e. salts whose cations are not toxic to the patient in pharmaceutical doses of the salts, such that the beneficial inhibitory effects inherent to the free base are not cancelled out by secondary effects due to the cations. Pharmaceutically acceptable salts, comprising those derived from alkaline-earth metal salts, within the scope of the invention comprise those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxy-methyl)aminomethane, tetramethylammonium hydroxide and the like.

The useful compounds according to the present invention may readily be prepared, or formed during the process of the invention, in the form of solvates (for example hydrates). The hydrates of the useful compounds according to the present invention may readily be prepared by recrystallisation from a mixture of aqueous/organic solvent, using organic solvents such as dioxane, tetrahydrofuran or methanol.

The base products or reagents used are commercially available and/or may be prepared by applying or adapting known processes, for example processes as described in the reference Examples or their obvious chemical equivalents.

According to the present invention, the compounds of the formula (I) exhibit selective ligand activity for the D3 receptor.

The present invention also provides pharmaceutical compositions comprising a compound according to the invention with a pharmaceutically acceptable vehicle or excipient.

Preferably, said composition contains an effective quantity of the compound according to the invention.

According to another object, the present invention also relates to the use of a compound of the general formula (I):

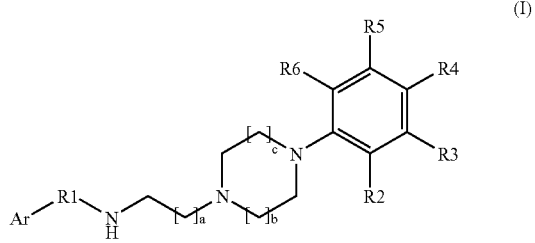

(I)

in which:

R1 represents a heteroaryl with five or six chain links, optionally containing one or more heteroatoms, selected from among 2-pyridyl, 2-pyrimidinyl, 2-pyridazinyl, 2-pyrazinyl, 2-imidazolyl, 2-oxazolyl, 2-thiazolyl, 3-isoxazolyl, 3-isothiazolyl, 1,2,4-triazol-2-yl, 1,3,4-oxadiazol-2-yl, 1,3,4-thiadiazol-2-yl, optionally substituted by one or more identical or different groups selected from among a halogen atom or a hydroxy, alkyl, monofluoroalkyl, polyfluoroalkyl, alkoxy, polyfluoroalkoxy, alkylsulfanyl, polyfluoroalkylsulfanyl group;

Ar is an aryl or heteroaryl, optionally fused with R1 and optionally substituted by one or more identical or different substituents selected from among a halogen atom or a hydroxy, alkyl, monofluoroalkyl, polyfluoroalkyl, alkoxy, polyfluoroalkoxy, alkylsulfanyl, polyfluoroalkylsulfanyl, cyano, carbamoyl, dialkylcarbamoyl, alkyl-C(=O)—, alkyl- O—C(=O)—, HO—C(=O)—, (HO)alkyl group, or Ar is fused with a saturated, unsaturated or aromatic hydrocarbon cycle or heterocycle;

a=2, 3 or 4;

b and c, identical or different, represent 1 or 2;

R2, R3, R4, R5 and R6 each independently represent a hydrogen or halogen atom or a hydroxy, alkyl, monofluoroalkyl, polyfluoroalkyl, alkoxy, polyfluoroalkoxy, alkylsulfanyl, polyfluoroalkylsulfanyl, cyano, —NRR', —COOR, —COR, —CONRR' group or alternatively two adjacent R2, R3, R4, R5 and R6 are joined to one another to form a hydrocarbon cycle or a saturated or unsaturated heterocycle, fused to the phenyl nucleus to which they are attached;

where R, R', identical or different, independently represent a hydrogen atom, or an alkyl group;

together with the stereoisomers or mixtures thereof, the tautomeric forms thereof, the hydrates, solvates thereof, the pharmaceutically acceptable salts and esters thereof, with the exception of those compounds for which:

R1 represents a 2-pyridyl group, fused to the group Ar=phenyl, a=2, b=c=1, R2=H, OMe and R3-R6=H or R2=R3=Me and R4-R6=H, for the preparation of pharmaceutical compositions intended to act as a ligand for the dopamine D3 receptor.

Preferably, said ligand is a D3 antagonist; still more preferably a selective D3 antagonist.

According to another object, the present invention also relates to the use of compounds of general formula (I) for the preparation of pharmaceutical compositions intended to prevent and/or treat a neuropsychiatric illness or any therapeutic illness involving the dopamine D3 receptor. Said illnesses are preferably selected from among drug dependency, sexual disorders, motor disorders, Parkinson's disease, psychosis or psychotic states, depression or drug dependency.

According to the invention, drug dependency is taken to mean any state associated with withdrawal, abstinence and/or detoxification of an individual dependent on any agent, in particular therapeutically active agents; such as opioids, and/or drugs such as cocaine, heroin, or alternatively alcohol and/or nicotine.

According to the invention, sexual disorders are in particular taken to mean impotence, in particular male impotence.

According to the invention, said prevention and/or treatment of Parkinson's disease is preferably an adjunct therapy for Parkinson's disease.

According to the invention, motor disorders are in particular taken to mean essential or iatrogenic dyskinesia, and/or essential or iatrogenic tremor.

According to another object, the present invention also relates to the above-mentioned therapeutic treatment methods comprising administration of a compound according to the invention to a patient who needs it.

Preferably, said composition is administered to a patient who needs it.

The pharmaceutical compositions according to the invention may assume forms intended for administration by parenteral, oral, rectal, permucosal or percutaneous routes.

They will therefore assume the form of injectable solutes or suspensions or multidose vials, of uncoated or coated tablets, sugar-coated tablets, capsules, gelatin capsules, pills, wafer capsules, powders, suppositories or rectal capsules, solutions or suspensions, for percutaneous use in a polar solvent, for permucosal use.

Suitable excipients for such administration forms are derivatives of cellulose or of microcrystalline cellulose, alkaline-earth carbonates, magnesium phosphate, starch, modified starch, lactose for solid forms.

For rectal use, cocoa butter or polyethylene glycol stearates are preferred excipients.

For parenteral use, water, aqueous solutes, physiological serum, isotonic solutes are the most conveniently used vehicles.

Dosage may vary within broad limits (0.5 mg to 1000 mg) depending not only on the therapeutic indication and route of administration, but also on the age and weight of the individual.

The following Examples illustrate the invention, but do not limit it. The starting products used are products which are known or prepared using known methods.

Unless otherwise stated, percentages are weight percentages.

EXAMPLES

Example 1

Preparation of 2-{4-[4-(2-fluorophenyl)piperazin-1-yl]butyl}amino-5-phenylpyridine

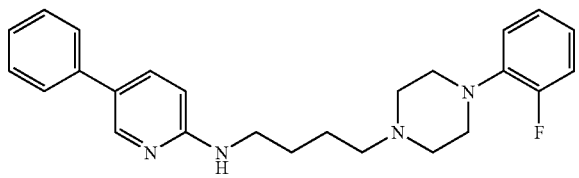

Step a: Preparation of 4-[4-(2-fluorophenyl)piperazin-1-yl]butyronitrile

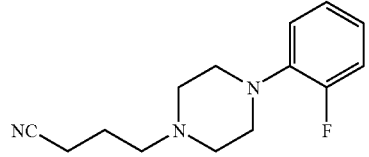

A spatula tipful of potassium iodide, 5.5 g (40 mmol) of potassium carbonate and 6.0 g (40 mmol) of 4-bromobutyronitrile are added in succession to a solution of 7.2 g (40 mmol) of 1-(2-fluorophenyl)piperazine in 100 mL of acetonitrile. The suspension is heated at reflux overnight.

The reaction medium is concentrated under a vacuum, and the residue is taken up with diethyl oxide and water. After separation of the aqueous phase, the organic phase is dried over magnesium sulfate, filtered and concentrated under a vacuum.

In this manner, 9.25 g (93%) of 4-[4-(2-fluorophenyl)piperazin-1-yl]butyronitrile are obtained in the form of a viscous oil which is used as it is in subsequent syntheses.

Step b: Preparation of 4-[4-(2-fluorophenyl)piperazin-1-yl]butylamine

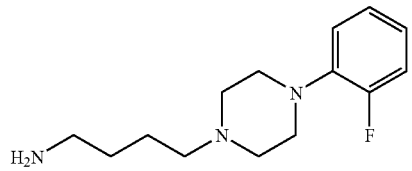

Approximately 1 g of Raney nickel washed beforehand with ethanol is added to a solution of 9.25 g (37.4 mmol) of 4-[4-(2-fluorophenyl)piperazin-1-yl]butyronitrile obtained previously, in a mixture of 50 mL of an aqueous solution of concentrated ammonia and 50 mL of an approx. 8N solution of ammoniacal ethanol.

The suspension is set to hydrogenate under 3 bar of hydrogen at 30° C. for 3 hours.

The mixture is filtered on celite, rinsed with ethanol and concentrated under a vacuum. The oily residue is taken up with 50 mL of ethanol and concentrated. This operation is repeated once.

In this manner, 8.8 g (94%) de 4-[4-(2-fluorophenyl)piperazin-1-yl]butylamine are obtained in the form of viscous oil which is used as it is in subsequent syntheses.

Step c: Preparation of 2-chloro-5-phenylpyridine

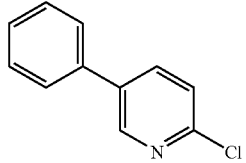

A solution of 0.7 g (5.7 mmol) of phenylboronic acid in 3 mL of ethanol is added to a mixture of 0.18 g (0.15 mmol) of tetrakis(triphenylphosphine)palladium, 1 g (5.15 mmol) of 5-bromo-2-chloropyridine, 5.7 mL of an aqueous solution of 2M sodium carbonate and 10 mL of toluene. The mixture is stirred vigorously and heated to 80° C. for 90 minutes.

After returning to ambient temperature, the reaction medium is extracted with 20 mL of ethyl acetate, then washed with 10 mL of water. The organic phase is dried over magnesium sulfate, filtered and concentrated under a vacuum. The chestnut brown oil obtained is purified by silica gel chromatography (elution with an ethyl acetate/heptane gradient) to produce 0.7 g (70%) of 2-chloro-5-phenylpyridine in the form of white crystals.

Rf=0.6 heptane/ethyl acetate 2/1 $^1$H NMR (DMSO d$_6$): 8.7 (multiplet, 1H); 8.1 (multiplet, 1H); 7.8 to 7.65 (unresolved peaks, 2H); 7.6 (multiplet, 1H); 7.55 to 7.35 (unresolved peaks, 3H)

Step d: Preparation of 2-{4-[4-(2-fluorophenyl)piperazin-1-yl]butyl}amino-5-phenylpyridine

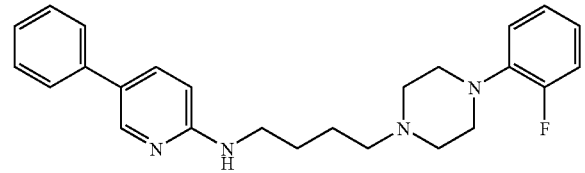

In a test tube, 0.189 g (1.0 mmol) of 2-chloro-5-phenylpyridine obtained previously and 0.25 g (1.0 mmol) of 4-[4-(2-fluorophenyl)piperazin-1-yl]butylamine (Example 1, step b) are heated for one minute in a microwave oven. The mixture is diluted with 3 mL of dichloromethane and chromatographed on silica gel (eluent: dichloromethane/ethanol 98/2).

After concentration of the elution fractions, the product crystallises. After comminution in diisopropyl oxide, filtration and drying, 20 mg of 2-{4-[4-(2-fluorophenyl)piperazin-1-yl]butyl}amino-5-phenylpyridine are obtained in the form of a cream solid.

Melting point: 95° C. $^1$H NMR (CDCl$_3$): 8.35 (singlet, 1H); 7.65 (doublet, 1H); 7.6 to 7.35 (unresolved peaks, 4H); 7.3 (multiplet, 1H); 7.15 to 6.85 (unresolved peaks, 4H); 6.45 (doublet, 1H); 4.95 to 4.7 (wide unresolved peaks, 1H); 3.35 (wide triplet, 2H); 3.2 to 3.0 (unresolved peaks, 4H); 2.85 to 2.65 (unresolved peaks, 4H); 2.5 (triplet, 2H); 1.85 to 2.5 (unresolved peaks, 4H)

Example 2

2-{4-[4-(2-fluorophenyl)piperazin-1-yl]butyl}amino-4-phenylpyridine

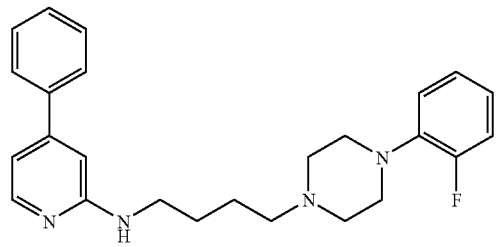

{2-{4-[4-(2-Fluorophenyl)piperazin-1-yl]butyl}amino-4-phenylpyridine is prepared by reacting 2-chloro-4-phenylpyridine (preparation described in EP 036 638) and 4-[4-(2-fluorophenyl)piperazin-1-yl]butylamine (Example 1, step b) using the same method as described in Example 1, step d.

Yield: 10% (red oil) $^1$H NMR: (CDCl$_3$): 8.1 (doublet, 1H); 7.7 to 7.5 (unresolved peaks, 2H); 7.5 to 7.3 (unresolved peaks, 3H); 7.1 to 6.85 (unresolved peaks, 4H); 6.8 (multiplet, 1H); 6.55 (singlet, 1H); 4.8 (wide singlet, 1H); 3.4 (wide triplet, 2H); 3.25 to 3.0 (unresolved peaks, 4H); 3.1 to 2.55 (unresolved peaks, 4H); 2.5 (triplet, 2H); 1.8 to 2.55 (unresolved peaks, 4H)

Example 3

2-{4-[4-(3-trifluoromethylphenyl)piperazin-1-yl]butyl}amino-4-phenylpyridine

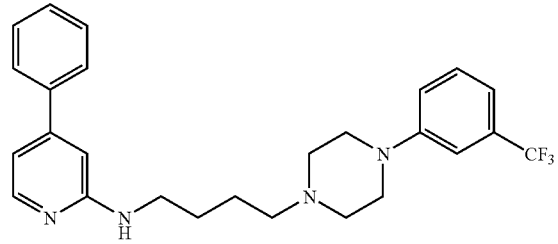

Step a: Preparation of 4-[4-(3-trifluoromethylphenyl)piperazin-1-yl]butyronitrile

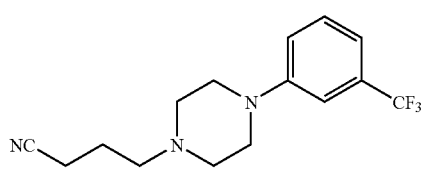

A mixture of 12.02 g (52 mmol) of 1-(3-trifluoromethylphenyl)piperazine, 7.9 g (57 mmol) of potassium carbonate, 8.5 g (57 mmol) of 4-bromobutyronitrile and 120 mL of acetonitrile is heated at reflux overnight.

The reaction medium is concentrated, taken up with ethyl acetate and washed with water. After separation of the aqueous phase, the organic phase is dried over magnesium sulfate, filtered and concentrated under a vacuum. In this manner, 15 g (97%) of 4-[4-(3-trifluoromethylphenyl)piperazin-1-yl]butyronitrile are obtained in the form of a viscous oil which is used as it is in subsequent syntheses.

Step b: Preparation of 4-[4-(3-trifluoromethylphenyl)piperazin-1-yl]butylamine

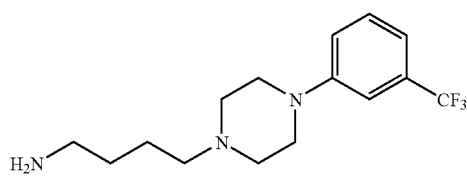

4-[4-(3-Trifluoromethylphenyl)piperazin-1-yl]butylamine may be obtained by reduction of 4-[4-(3-trifluoromethylphenyl)piperazin-1-yl]butyronitrile using the same method as that used in Example 1, step b.

Yield: 92% (viscous oil)

The product is used in its crude state in the following step.

Step c: Preparation of 2-{4-[4-(3-trifluoromethylphenyl)piperazin-1-yl]butyl}amino-4-phenylpyridine

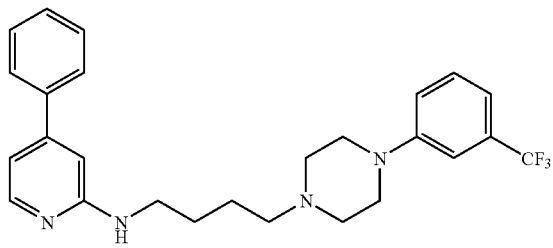

In a test tube, 0.38 g (2.0 mmol) of 2-chloro-4-phenylpyridine, 0.6 g (2.0 mmol) of 4-[4-(3-trifluoromethylphenyl)piperazin-1-yl]butylamine and a spatula tipful of 4-dimethylaminopyridine are heated to approximately 300-350° C. for 3 minutes. The mixture is diluted with ethyl acetate and chromatographed on silica gel (eluent: dichloromethane/ethanol 90/10).

After concentration of the elution fractions, the product crystallises. After comminution in diethyl oxide, filtration and drying, 80 mg of 2-{4-[4-(3-trifluoromethylphenyl)piperazin-1-yl]butyl}amino-4-phenylpyridine are obtained in the form of a white solid.

Melting point: 120° C. (tube) $^1$H NMR (CDCl$_3$): 8.1 (doublet, 1H); 7.65 to 7.55 (unresolved peaks, 2H); 7.5 to 7.25 (unresolved peaks, 4H); 7.2 to 7.0 (unresolved peaks, 3H); 6.8 (doublet, 1H); 6.55 (singlet, 1H); 4.8 (wide triplet, 1H); 3.35 (multiplet, 2H); 3.35 to 3.15 (unresolved peaks, 4H); 2.7 to 2.55 (unresolved peaks, 4H); 2.45 (triplet, 2H); 1.85 to 1.65 (unresolved peaks, 4H)

Example 4

Preparation of 2-{4-[4-(3-trifluoromethyl-phenyl)piperazin-1-yl]butyl}amino-4-phenylpyridine dihydrochloride

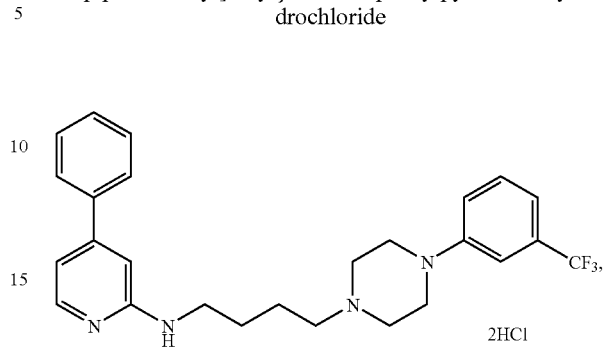

0.5 mL of a saturated solution of hydrogen chloride in diethyl oxide is added at ambient temperature to a solution of 0.15 g (0.33 mmol) of 2-{4-[4-(3-trifluoro-methylphenyl)piperazin-1-yl]butyl}amino-4-phenylpyridine (Example 3) in 5 mL of acetone. Precipitation is immediate. The suspension is stirred for 15 minutes, filtered and dried under a vacuum down to a constant mass. In this manner, 0.12 g of 2-{4-[4-(3-trifluoromethylphenyl)piperazin-1-yl]butyl}amino-4-phenylpyridine dihydrochloride are obtained in the form of white solid.

Melting point: 217° C. $^1$H NMR (DMSO d$_6$): 13.8 (wide singlet, 1H); 11.0 (wide singlet, 1H); 9.1 (wide singlet, 1H); 7.95 (doublet, 1H); 7.9 to 7.7 (unresolved peaks, 2H); 7.6 to 7.5 (unresolved peaks, 3H); 7.5 to 7.3 (unresolved peaks, 2H); 7.3 to 1.05 (unresolved peaks, 4H); 3.95 (wide triplet, 2H); 3.7 to 3.55 (unresolved peaks, 4H); 3.55 to 2.9 (unresolved peaks, 6H); 2.0 to 1.8 (unresolved peaks, 2H); 1.8 to 1.5 (unresolved peaks, 2H)

Example 5

Preparation of 2-{4-[4-(3-trifluoromethylphenyl)piperazin-1-yl]butyl}amino-5-phenylpyridine

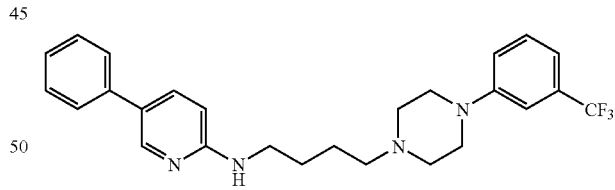

2-{4-[4-(3-Trifluoromethylphenyl)piperazin-1-yl]butyl}amino-5-phenyl-pyridine may be obtained by reaction of 2-chloro-5-phenylpyridine (Example 1, step c) with 4-[4-(3-trifluoromethylphenyl)piperazin-1-yl]butylamine (Example 3, step b) using the same method as that described in Example 3, step c.

Yield: 12% Melting point: 115° C. (tube) $^1$H NMR (DMSO d$_6$): 8.25 (singlet, 1H); 7.65 (doublet, 1H); 7.55 to 7.4 (unresolved peaks, 2H); 7.45 to 7.3 (unresolved peaks, 3H); 7.3 to 7.15 (unresolved peaks, 2H); 7.1 (singlet, 1H); 7.0 (doublet, 1H); 6.65 (triplet, 1H); 6.5 (doublet, 1H); 3.3 (wide triplet, 2H); 3.2 to 3.05 (unresolved peaks, 4H); 2.55 to 2.4 (unresolved peaks, 4H); 2.3 (wide triplet, 2H); 1.65 to 1.4 (unresolved peaks, 4H)

Example 6

Preparation of 2-{4-[4-(2,3-dichlorophenyl)piperazin-1-yl]butyl}amino-4-phenylpyridine

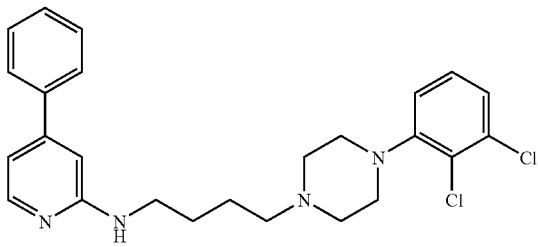

Step a: Preparation of 4-[4-(2,3-dichlorophenyl)piperazin-1-yl]butyronitrile

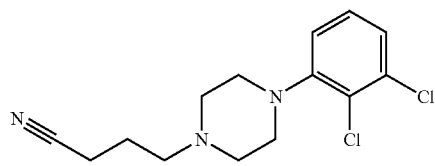

4-[4-(2,3-Dichlorophenyl)piperazin-1-yl]butyronitrile may be obtained by alkylating 1-(2,3-dichlorophenyl)piperazine hydrochloride with 4-bromobutyronitrile using the same method as in Example 1, step a.

Yield: 65% (viscous oil). The product is used in its crude state in the following step.

Step b: Preparation of 4-[4-(2,3-dichlorophenyl)piperazin-1-yl]butylamine

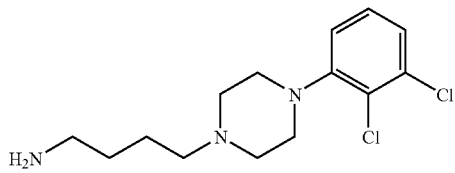

4-[4-(2,3-Dichlorophenyl)piperazin-1-yl]butylamine may be obtained by reduction of 4-[4-(2,3-dichlorophenyl)piperazin-1-yl]butyronitrile using the same method as that used in Example 1, step b.

Yield: 91% (viscous oil)

The product is used in its crude state in the following step.

Step c: Preparation of 2-{4-[4-(2,3-fluorophenyl)piperazin-1-yl]butyl}amino-4-phenylpyridine

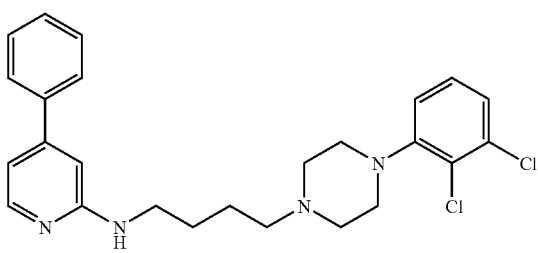

In a test tube, 0.19 g (2.0 mmol) of 2-chloro-4-phenylpyridine, 0.3 g (1.0 mmol) of 4-[4-(2,3-dichlorophenyl)piperazin-1-yl]butylamine and a spatula tipful of 4-dimethylaminopyridine are heated for 4 minutes in a microwave oven. The mixture is diluted with ethyl acetate and chromatographed on silica gel (eluent: ethyl acetate/ethanol).

After concentration of the elution fractions, 20 mg (4%) of 2-{4-[4-(2,3-dichlorophenyl)piperazin-1-yl]butyl}amino-4-phenylpyridine are obtained in the form of a yellowish viscous oil.

$^1$H NMR (CDCl$_3$): 8.15 (doublet, 1H); 7.65 to 7.5 (unresolved peaks, 2H); 7.5 to 7.35 (unresolved peaks, 3H); 7.2 to 7.05 (unresolved peaks, 2H); 6.9 (multiplet, 1H); 6.75 (multiplet, 1H); 6.55 (singlet, 1H); 4.9 (wide singlet, 1H); 3.4 (triplet, 2H); 3.2 to 3.0 (unresolved peaks, 4H); 2.8 to 2.5 (unresolved peaks, 4H); 2.5 (triplet, 2H); 1.8 to 1.6 (unresolved peaks, 4H)

Example 7

Preparation of 2-{4-[4-(2,3-dichlorophenyl)piperazin-1-yl]butyl}amino-5-phenylpyridine

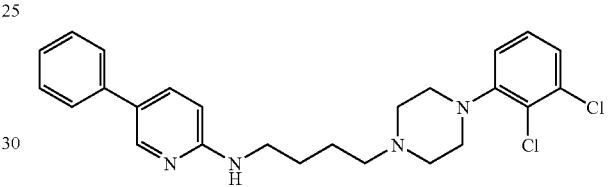

In a test tube, 0.2 g (1.0 mmol) of 2-chloro-5-phenylpyridine (Example 1, step c), 0.3 g (1.0 mmol) of 4-[4-(2,3-dichlorophenyl)piperazin-1-yl]butylamine (Example 6, step b) are heated to 300-350° C. for 4 minutes. The mixture is diluted with ethyl acetate and chromatographed on silica gel (eluent: ethyl acetate/methanol).

After concentration of the elution fractions, the precipitate is comminuted in diethyl oxide, filtered and dried under a vacuum. In this manner, 20 mg (4%) of 2-{4-[4-(2,3-dichlorophenyl)piperazin-1-yl]butyl}amino-5-phenylpyridine are obtained in the form of a white solid.

Melting point: 110° C. (tube) $^1$H NMR (DMSO d$_6$): 8.25 (singlet, 1H); 7.6 (doublet, 1H); 7.55 to 7.45 (multiplet, 2H); 7.4 to 7.3 (multiplet, 2H); 7.3 to 7.15 (multiplet, 2H) 7.15 to 7.5 (multiplet, 1H); 6.6 (triplet, 1H); 6.5 (doublet, 1H); 5.7 (singlet, 1H); 3.4 to 3.2 (unresolved peaks, 4H); 3.1 (wide triplet, 2H); 3.0 to 2.85 (unresolved peaks, 4H); 2.3 (wide triplet, 2H); 1.6 to 1.4 (unresolved peaks, 4H)

Example 8

Preparation of 2-{4-[4-(2,3-dichlorophenyl)piperazin-1-yl]butyl}amino-5-(2-methylphenyl)pyridine

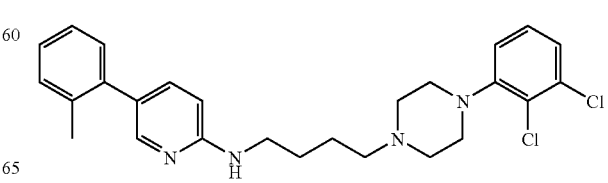

Step a: Preparation of 2-chloro-5-(2-methylphenyl)pyridine

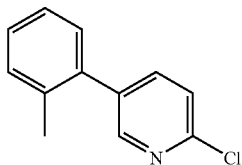

2-Chloro-5-(2-methylphenyl)pyridine may be prepared by a Suzuki reaction starting from 2-chloro-5-bromopyridine and 2-methyl-phenylboronic acid using the same method as that described in Example 1, step c.

Yield: 47% (crystalline product) $^1$H NMR (CDCl$_3$): 8.4 (singlet, 1H); 7.6 (multiplet, 1H); 7.5 to 7.1 (unresolved peaks, 5H); 2.25 (singlet, 3H)

Step b: Preparation of 2-{4-[4-(2,3-dichlorophenyl)piperazin-1-yl]butyl}amino-5-(2-methylphenyl)pyridine

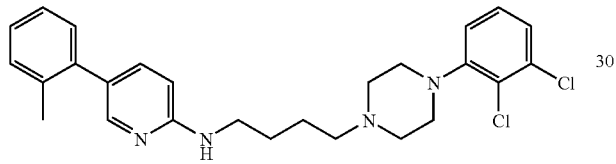

2-{4-[4-(2,3-Dichlorophenyl)piperazin-1-yl]butyl}amino-5-(2-methyl-phenyl)-pyridine may be prepared from 2-chloro-5-(2-methylphenyl)pyridine obtained previously and 4-[4-(2,3-dichloro-phenyl)piperazin-1-yl]butylamine (Example 6, step b) using the same process as that described in Example 7.

Yield: 7% (orange oil) $^1$H NMR (CDCl$_3$): 8.05 (singlet, 1H); 7.4 (doublet, 1H); 7.3 to 7.05 (unresolved peaks, 6H); 6.95 (multiplet, 1H); 6.45 (doublet, 1H); 4.85 (wide singlet, 1H); 3.35 (wide triplet, 2H); 3.2 to 3.0 (unresolved peaks, 4H); 2.8 to 2.55 (unresolved peaks, 4H); 2.5 (triplet, 2H); 2.3 (singlet, 3H); 1.8 to 1.6 (unresolved peaks, 4H)

Example 9

Preparation of 2-{4-[4-(3-trifluoromethylphenyl)piperazin-1-yl]butyl}amino-5-(2-methylphenyl)pyridine

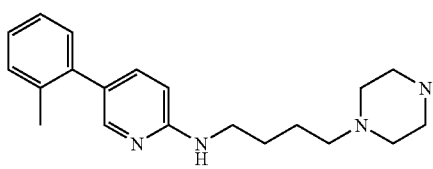

2-{4-[4-(3-Trifluoromethylphenyl)piperazin-1-yl]butyl}amino-5-(2-methyl-phenyl)pyridine may be prepared from 2-chloro-5-(2-methyl-phenyl)pyridine (Example 8, step a) and 4-[4-(3-trifluoro-methylphenyl)piperazin-1-yl]butylamine (Example 3, step b) using the same process as that described in Example 7.

Yield: 7% (orange oil) $^1$H NMR (CDCl$_3$): 8.05 (doublet, 1H); 7.5 to 7.0 (unresolved peaks, 9H); 6.45 (doublet, 1H); 4.85 (wide singlet, 1H); 3.35 (wide triplet, 2H); 3.3 to 3.15 (unresolved peaks, 4H); 2.75 to 2.55 (unresolved peaks, 4H); 2.5 (triplet, 2H); 2.3 (singlet, 3H); 1.9 to 1.55 (unresolved peaks, 4H)

Example 10

Preparation of 2-{4-[4-(3-trifluoromethylphenyl)piperazin-1-yl]butyl}amino-5-(4-fluorophenyl)pyridine

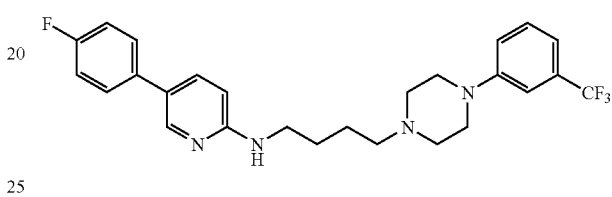

Step a: Preparation of 2-chloro-5-(4-fluorophenyl)pyridine

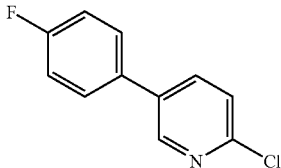

2-Chloro-5-(4-fluorophenyl)pyridine may be prepared by a Suzuki reaction from 2-chloro-5-bromopyridine and 4-fluoro-phenylboronic acid using the same method as that described in Example 1, step c.

Yield: 74% (crystalline product) $^1$H NMR (CDCl$_3$): 8.9 (singlet, 1H); 8.55 (doublet, 1H); 8.05 (doublet, 1H); 7.8 to 7.5 (multiplet, 2H); 7.35 to 7.05 (multiplet, 2H)

Step b: Preparation of 2-{4-[4-(3-trifluoromethylphenyl)piperazin-1-yl]butyl}amino-5-(4-fluorophenyl)pyridine

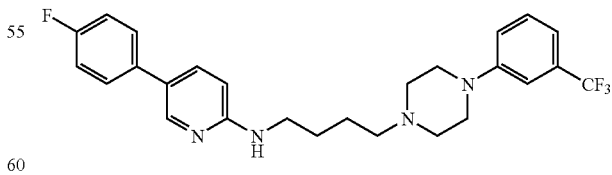

2-{4-[4-(3-Trifluoromethylphenyl)piperazin-1-yl]butyl}amino-5-(4-fluoro-phenyl)pyridine may be prepared from 2-chloro-5-(4-fluoro-phenyl)pyridine obtained previously and 4-[4-(3-trifluoromethyl-phenyl)piperazin-1-yl]butylamine (Example 3, step b) using the same method as that described in Example 7.

Yield: 4% (red viscous oil) $^1$H NMR (CDCl$_3$): 8.3 (doublet, 1H); 7.65 to 7.55 (unresolved peaks, 2H); 7.5 to 7.2 (unresolved peaks, 3H); 7.2 to 7.0 (unresolved peaks, 4H); 6.45 (doublet, 1H); 4.9 (wide singlet, 1H); 3.35 (triplet, 2H); 3.3 to 3.1 (unresolved peaks, 4H); 2.7 to 2.5 (unresolved peaks, 4H); 2.5 (triplet, 2H); 1.85 to 1.5 (unresolved peaks, 4H)

Example 11

Preparation of 2-{4-[4-(3-trifluoromethylphenyl)piperazin-1-yl]butyl}amino-4-(2-methylphenyl)pyridine

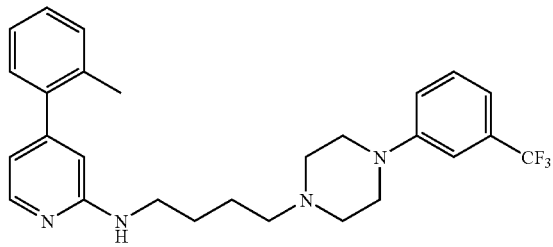

Step a: Preparation of 4-(2-methylphenyl)pyridine N-oxide

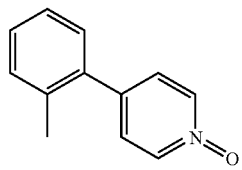

A mixture of 10 mL of toluene, 0.268 g (0.23 mmol) of tetrakis(triphenylphosphine)palladium, 0.776 g (5.71 mmol) of 2-methyl-phenylboronic acid, 2.85 mL (5.71 mmol) of a 2M aqueous sodium carbonate solution and 0.737 g (5.19 mmol) of 4-chloropyridine N-oxide is heated at reflux for 4 hours.

The reaction medium is then concentrated under a vacuum and taken up with ethyl acetate. The organic phase is washed with water, dried over magnesium sulfate, filtered and concentrated under a vacuum. The residue is chromatographed on silica gel (elution with a 95/5 mixture of dichloromethane/ethanol). In this manner 0.6 g (56%) of 4-(2-methylphenyl)-pyridine N-oxide is obtained, which is used as it is in the subsequent syntheses.

Step b: Preparation of 2-chloro-4-(2-methylphenyl)pyridine

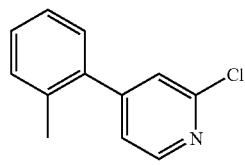

A mixture of 0.6 g (3.24 mmol) 4-(2-methyl-phenyl)pyridine N-oxide obtained previously, 1.8 g (31 mmol) of sodium chloride and 3.3 mL (35.5 mmol) of phosphorus oxychloride is heated at reflux overnight.

The reaction medium is then concentrated under a vacuum. The residue is diluted in toluene and again concentrated under a vacuum. The oily residue is cooled to approximately 5° C., alkalised to pH=9 with a normal aqueous solution of sodium hydroxide and then extracted with ethyl acetate. The organic phase is washed with water, dried over magnesium sulfate, filtered and concentrated under a vacuum. The oily residue is chromatographed on silica gel (elution with a 3/1 mixture of heptane/ethyl acetate). In this manner, 0.5 g (74%) of 2-chloro-4-(2-methylphenyl)pyridine is obtained in the form of a coloured oil which is used as it is in subsequent syntheses.

Step c: Preparation of 2-{4-[4-(3-trifluoromethylphenyl)piperazin-1-yl]butyl}amino-4-(2-methylphenyl)pyridine

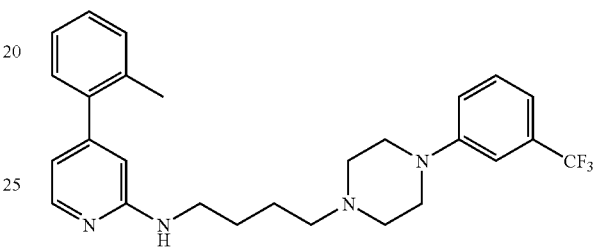

2-{4-[4-(3-Trifluoromethylphenyl)piperazin-1-yl]butyl}amino-4-(2-methyl-phenyl)pyridine may be obtained from 2-chloro-4-(2-methyl-phenyl)pyridine prepared previously and 4-[4-(3-trifluoromethyl-phenyl)piperazin-1-yl]butylamine (Example 3, step b) using the same method as that described in Example 3, step c.

Yield: 10% (reddish oil) $^1$H NMR (CDCl$_3$): 8.1 (doublet, 1H); 7.35 to 7.15 (unresolved peaks, 5H); 7.15 to 6.95 (unresolved peaks, 3H); 6.55 (doublet, 1H); 6.35 (singlet, 1H); 5.15 (wide singlet, 1H); 3.3 to 3.15 (unresolved peaks, 4H); 3.35 (wide triplet, 2H); 2.8 to 2.6 (unresolved peaks, 4H); 2.5 (triplet, 2H); 2.3 (singlet, 3H); 1.85 to 1.6 (unresolved peaks, 4H)

Example 12

Preparation of 2-{4-[4-(2,3-dichloromethylphenyl)piperazin-1-yl]butyl}amino-4-(2-methylphenyl)pyridine

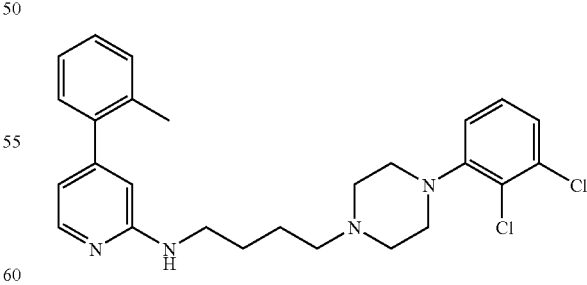

2-{4-[4-(2,3-Dichloromethylphenyl)piperazin-1-yl]butyl}amino-4-(2-methyl-phenyl)pyridine may be prepared from 2-chloro-4-(2-methyl-phenyl)pyridine (Example 11, step b) and 4-[4-(2,3-dichlorophenyl)piperazin-1-yl]butylamine (Example 6, step b) using the same process as that described in Example 7.

Yield: 7% (orange oil) ¹H NMR (CDCl₃): 8.1 (doublet, 1H); 7.3 to 7.1 (unresolved peaks, 6H); 6.95 (multiplet, 1H); 6.55 (doublet, 1H); 6.3 (singlet, 1H); 4.8 (wide singlet, 1H); 3.3 (triplet, 2H); 3.15 to 3.0 (unresolved peaks, 4H); 2.7 to 2.5 (unresolved peaks, 4H); 2.45 (triplet, 2H); 2.3 (singlet, 3H); 1.8 to 1.55 (unresolved peaks, 4H)

Example 13

Preparation of 2-{4-[4-(2-cyano-3-trifluoromethyl-phenyl)piperazin-1-yl]butyl}amino-4-phenylpyridine

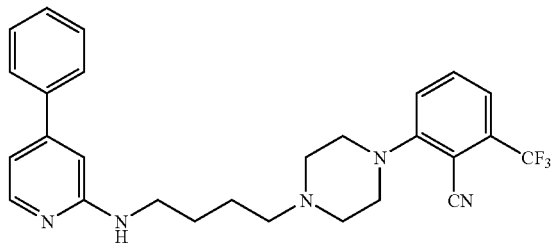

Step a: Preparation of 4-(2-cyano-3-trifluoromethylphenyl)piperazine

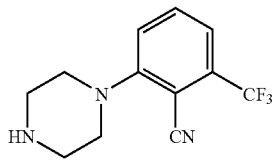

A mixture of 3 g (15.8 mmol) of 2-fluoro-6-trifluoromethylbenzonitrile, 7.5 g (87 mmol) of piperazine and 24 mL of dioxane is heated at reflux for 5 hours.

The reaction medium is concentrated under a vacuum and the residue is taken up with ethyl acetate. After washing with water, the organic phase is dried over magnesium sulfate, filtered and concentrated. The product crystallises at ambient temperature. After drying under a vacuum, 3.6 g (82%) of 4-(2-cyano-3-trifluoromethylphenyl)piperazine are obtained, this being used as it is in subsequent syntheses.

Step b: Preparation of 2-{4-[4-(2-cyano-3-trifluoromethylphenyl)piperazin-1-yl]butyl}phthalimide

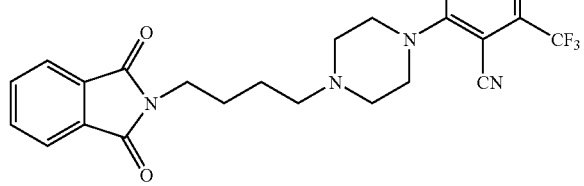

A mixture of 2.55 g (10 mmol) of 4-(2-cyano-3-trifluoromethylphenyl)piperazine prepared previously, 1.5 g (10.9 mmol) of potassium carbonate, 3.1 g (10.9 mmol) of N-(4-bromobutyl)phthalimide and 30 mL of acetonitrile is heated at reflux overnight.

The reaction medium is then concentrated under a vacuum, after which it is taken up with ethyl acetate. After washing with water, the organic phase is dried over magnesium sulfate, filtered and concentrated under a vacuum. The oily residue is stirred with diisopropyl oxide. The supernatant is removed and the residue is dried under a vacuum. In this manner, 3.8 g (100%) of 2-{4-[4-(2-cyano-3-trifluoro-methylphenyl)piperazin-1-yl]butyl}phthalimide are obtained in the form of a viscous oil which is used as it is in subsequent syntheses.

Step c: Preparation of 4-(4-aminobutyl)-1-(2-cyano-3-trifluoromethyl-phenyl)piperazine

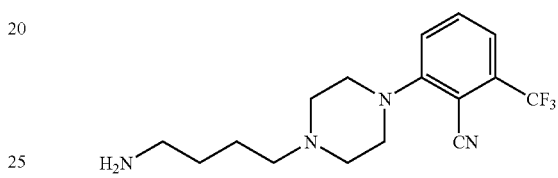

A solution of 1 g (2.57 mmol) of 2-{4-[4-(2-cyano-3-trifluoro-methylphenyl)piperazin-1-yl]butyl}phthalimide prepared previously and 1 mL of hydrazine hydrate in 10 mL of ethanol is stirred overnight at ambient temperature.

The solution is concentrated under a vacuum. The residue is taken up with water, again concentrated under a vacuum, acidified to pH 1 with a 0.5 N aqueous solution of hydrochloric acid and washed with ethyl acetate. The aqueous phase is cooled. A normal aqueous sodium hydroxide solution is added up to pH 9. The basic aqueous phase is extracted twice with ethyl acetate. The extraction phases are combined, washed with water, dried over magnesium sulfate, filtered and concentrated. In this manner, 0.7 g (83%) of 4-(4-aminobutyl)-1-(2-cyano-3-trifluoromethylphenyl)piperazine are obtained in the form of an oil which is used as it is in subsequent syntheses.

Step d: Preparation of 2-{4-[4-(2-cyano-3-trifluoromethyl-phenyl)piperazin-1-yl]butyl}amino-4-phenylpyridine

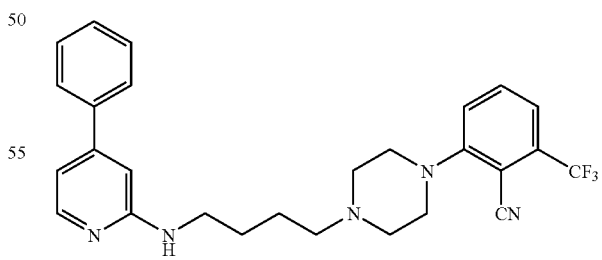

2-{4-[4-(2-Cyano-3-trifluoromethylphenyl)piperazin-1-yl]butyl}amino-4-phenylpyridine may be obtained from 4-(4-aminobutyl)-1-(2-cyano-3-trifluoromethylphenyl)piperazine prepared previously and 2-chloro-4-phenylpyridine using the same method as that described in Example 3, step c.

Yield: 4% (cream solid) Melting point: 102° C. (tube) ¹H NMR (CDCl₃): 8.1 (doublet, 1H); 7.7 to 7.5 (unresolved peaks, 3H); 7.5 to 7.35 (unresolved peaks, 3H); 7.3 (doublet, 1H); 7.2 (multiplet, 1H); 6.8 (doublet, 1H); 6.55 (singlet, 1H); 4.95 to 4.7 (wide singlet, 1H); 3.35 (wide triplet, 2H); 3.3 to 3.2 (unresolved peaks, 4H); 2.8 to 2.6 (unresolved peaks, 4H); 2.5 (triplet, 2H); 1.85 to 1.6 (unresolved peaks, 4H)

Example 14

Preparation of 2-{5-[4-(3-trifluoromethyl-phenyl)piperazin-1-yl]pentyl}-amino-4-phenylpyridine dihydrochloride

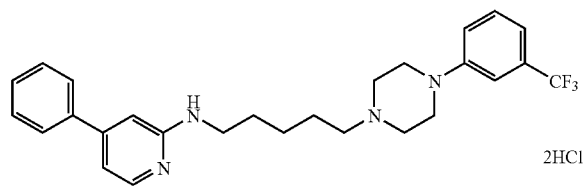

Step a: Preparation of 2-chloro-4-phenylpyridine-1-oxide

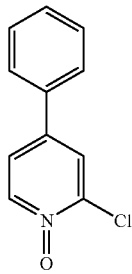

10.73 g (62.2 mmol) of meta-chloroperbenzoic acid are added in portions to a solution of 3.3 g (17.4 mmol) of 2-chloro-4-phenylpyridine in 35 mL of dichloromethane cooled to 5° C. The suspension is stirred overnight at ambient temperature.

The reaction medium is diluted with 150 mL of ethyl acetate and washed successively with water, with a saturated aqueous sodium metabisulfite solution, with a saturated aqueous sodium carbonate solution and with water.

The organic phase is then dried over magnesium sulfate, filtered and concentrated.

The solid residue is stirred with an acetonitrile/diisopropyl oxide mixture, filtered and dried under a vacuum.

Yield: 51% Melting point: 152° C. $^1$H NMR (CDCl$_3$): 8.4 (doublet, 1H, J=6.7 Hz); 7.7 (d, 1H, J=2.5 Hz); 7.65 to 7.35 (unresolved peaks, 6H).

Step b: Preparation of 2-{5-[4-(3-trifluoromethylphenyl)piperazin-1-yl]pentyl}-amino-4-phenylpyridine-1-oxide

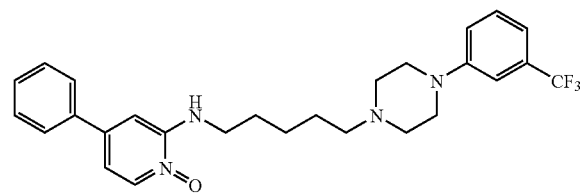

0.75 g (2.4 mmol) of 3-[5-(3-trifluoromethylphenyl)piperazin-1-yl]pentylamine and 0.18 g (2.2 mmol) of sodium hydrogencarbonate are added to a solution of 0.41 g (2 mmol) of 2-chloro-4-phenylpyridine-1-oxide in 5 mL of tert.-amyl alcohol. The mixture is heated at reflux overnight.

After concentration under a vacuum, the residue is taken up with ethyl acetate and washed twice with water. The organic phase is dried over magnesium sulfate, filtered and concentrated. The resultant oil is purified by silica gel chromatography (eluent: dichloromethane/methanol 98/2).

Yield: 66% (chestnut brown viscous oil). $^1$H NMR (CDCl$_3$): 8.15 (d, 1H, J=6.7 Hz); 7.65 to 7.55 (unresolved peaks, 2H); 7.55 to 7.3 (unresolved peaks, 4H); 7.2 to 7.0 (unresolved peaks, 3H); 6.9 to 6.7 (unresolved peaks, 3H); 3.35 (multiplet, 2H, J=6 Hz); 3.25 (multiplet, 4H); 2.6 (multiplet, 4H); 2.4 (triplet, 2H, J=7 Hz); 1.9 to 1.4 (unresolved peaks, 6H)

Step c: Preparation of 2-{5-[4-(3-trifluoromethyl-phenyl)piperazin-1-yl]pentyl}-amino-4-phenylpyridine dihydrochloride

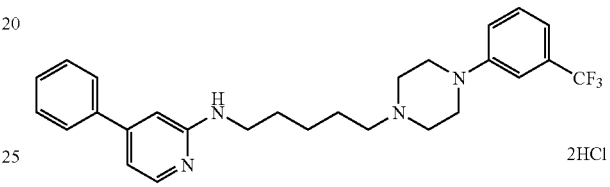

A solution of 0.51 g (1.05 mmol) of 2-{5-[4-(3-trifluoromethylphenyl)piperazin-1-yl]pentyl}amino-4-phenylpyridine-1-oxide in 5 mL of chloroform is cooled to 5° C. After addition of 0.2 mL (2.3 mmol) of phosphorus trichloride, the reaction medium is stirred overnight at ambient temperature.

The mixture is concentrated under a vacuum and is then hydrolysed with 10 mL of water and 2 mL of a 1N aqueous sodium hydroxide solution. The product is extracted with ethyl acetate (two 25 mL portions). The organic phases are combined, dried over magnesium sulfate, filtered and concentrated. The resultant oil is purified by silica gel chromatography (eluent: dichloromethane/methanol 98/2).

The resultant oil is dissolved in diethyl oxide. A saturated solution of hydrogen chloride in diethyl oxide is added until a precipitate is obtained. The solid is filtered, washed with ethyl acetate and dried under a vacuum.

White solid. Melting point: 94° C. $^1$H NMR (CDCl$_3$): 8.15 (d, 1H, J=5 Hz); 7.7 to 7.55 (unresolved peaks, 2H); 7.55 to 7.25 (unresolved peaks, 4H); 7.2 to 7.0 (unresolved peaks, 3H); 6.8 (doublet, 1H, J=5 Hz); 6.6 (singlet, 1H); 4.6 (wide triplet, 1H); 3.4 (multiplet, 2H); 3.2 (multiplet, 4H); 2.6 (multiplet, 4H); 2.4 (triplet, 2H, J=7 Hz); 1.8 to 1.4 (unresolved peaks, 6H)

The products of Examples 15 to 20 are prepared using the same reaction sequence as that described in Example 14.

Example 15

Preparation of 2-{4-[4-(1,2-dimethylphenyl)-piperazin-1-yl]butyl}-amino-4-phenylpyridine

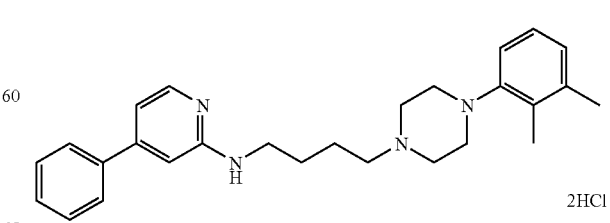

The chestnut brown oil obtained after the reduction step with phosphorus trichloride (see Example 14, step c) is dissolved in diethyl oxide. A saturated solution of hydrogen chloride in diethyl oxide is added until a precipitate is obtained. The solid is filtered, washed with ethyl acetate and dried under a vacuum.

White solid.

Melting point: 101° C. $^1$H NMR (DMSO D$_6$): 8.0 (doublet, 1H, J=6.7 Hz); 7.85 to 7.7 (unresolved peaks, 2H); 7.65 to 7.5 (unresolved peaks, 3H); 7.35 (singlet, 1H); 7.2 (doublet, 1H, J=5 Hz); 7.05 (triplet, 1H, J=6.7 Hz); 6.95 to 6.8 (unresolved peaks, 2H); 3.5 (multiplet, 4H); 3.2 to 3.0 (unresolved peaks, 8H); 2.2 (singlet, 3H); 2.15 (singlet, 3H); 2.0 to 1.75 (unresolved peaks, 2H); 1.75 to 1.55 (unresolved peaks, 2H)

Example 16

Preparation of 2-{4-[4-(2-cyano-3-methylphenyl)piperazin-1-yl]butyl}-amino-4-phenylpyridine

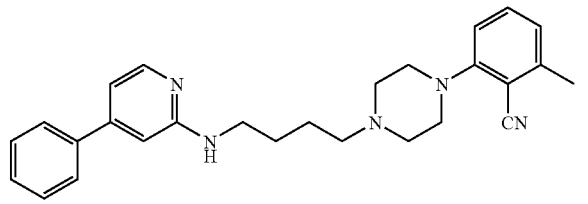

Light chestnut brown oil $^1$H NMR (CDCl$_3$): 8.1 (doublet, 1H, J=5 Hz); 7.7 to 7.55 (unresolved peaks, 2H); 7.55 to 7.3 (unresolved peaks, 4H); 6.95 to 6.75 (unresolved peaks, 3H); 6.6 (singlet, 1H); 5.5 (wide singlet, 1H); 3.4 (multiplet, 2H); 3.2 (multiplet, 4H); 2.7 (multiplet, 4H); 2.65 to 2.4 (unresolved peaks, 5H); 1.85 to 1.6 (unresolved peaks, 4H)

Example 17

Preparation of 2-{4-[4-(3,5-dichlorophenyl)piperazin-1-yl]butyl}-amino-4-phenylpyridine

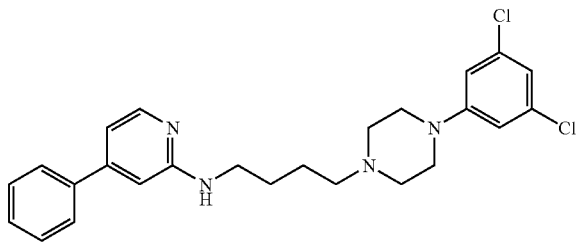

White solid. Melting point: 108° C. $^1$H NMR (CDCl$_3$): 8.1 (doublet, 1H, J=5 Hz); 7.75 to 7.55 (unresolved peaks, 2H); 7.55 to 7.35 (unresolved peaks, 3H); 6.85 to 6.7 (unresolved peaks, 4H); 6.5 (singlet, 1H); 4.9 (wide singlet, 1H); 3.4 (multiplet, 2H); 3.2 (multiplet, 4H); 2.6 (multiplet, 4H); 2.45 (triplet, 2H, J=6.7 Hz); 1.85 to 1.6 (unresolved peaks, 4H)

Example 18

Preparation of 2-{4-[4-(3-chlorophenyl)piperazin-1-yl]butyl}amino-4-phenylpyridine

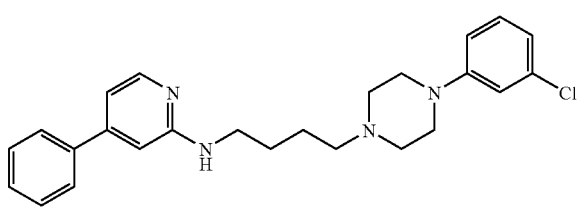

White solid. Melting point: 104° C. $^1$H NMR (CDCl$_3$): 8.1 (doublet, 1H, J=5 Hz); 7.7 to 7.55 (unresolved peaks, 2H); 7.55 to 7.35 (unresolved peaks, 3H); 7.2 (triplet, 1H, J=7 Hz); 6.9 (singlet, 1H); 6.9 to 6.75 (unresolved peaks, 3H); 6.55 (singlet, 1H); 4.8 (wide singlet, 1H); 3.35 (multiplet, 2H); 3.2 (multiplet, 4H); 2.6 (multiplet, 4H); 2.45 (triplet, 2H, J=6.7 Hz); 1.85 to 1.5 (unresolved peaks, 4H)

Example 19

Preparation of 2-{4-[4-(5,6,7,8-tetrahydro-1-naphthyl)piperazin-1-yl]butyl}amino-4-phenylpyridine dihydrochloride

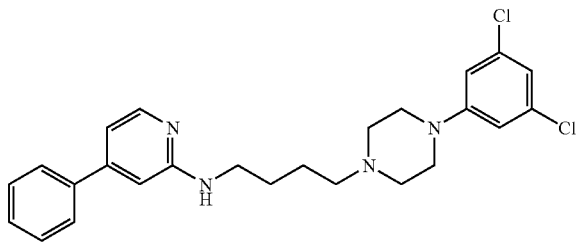

White solid Melting point: 168° C. $^1$H NMR (DMSO D$_6$): 8.0 (doublet, 1H, J=7 Hz); 7.7 to 7.55 (unresolved peaks, 2H); 7.55 to 7.35 (unresolved peaks, 3H); 7.1 (triplet, 1H, J=7 Hz); 6.9 to 7.65 (unresolved peaks, 4H); 3.55 to 3.2 (unresolved peaks, 6H); 3.2 to 2.95 (unresolved peaks, 6H); 2.8 to 2.55 (unresolved peaks, 4H); 1.85 to 1.45 (unresolved peaks, 8H)

Example 20

Preparation of 2-{4-[4-(2-cyano-3-isopropoxyphenyl)piperazin-1-yl]-butyl}amino-4-phenylpyridine

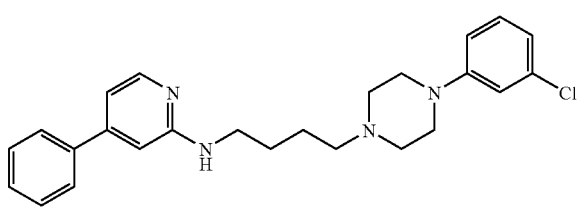

Yellow crystalline solid Melting point: 148° C. $^1$H NMR (CDCl$_3$): 8.1 (doublet, 1H, J=5 Hz); 7.65 to 7.55 (unresolved peaks, 2H); 7.5 to 7.35 (unresolved peaks, 3H); 7.3 (triplet, 1H, J=7 Hz); 6.8 (multiplet, 1H); 6.65 to 6.45 (unresolved peaks, 3H); 5.0 (wide singlet, 1H); 4.6 (septuplet, 1H, J=6 Hz); 3.35 (multiplet, 2H); 3.25 (multiplet, 4H); 2.7 (multiplet, 4H); 2.5 (triplet, 1H, J=7 Hz); 1.85 to 1.6 (unresolved peaks, 4H); 1.4 (doublet, 6H, J=6 Hz)

Example 21

Preparation of 2-{4-[4-(3-trifluoromethylphenyl)piperazin-1-yl]butyl}-amino-4-(4-fluorophenyl)pyridine

Step a: Preparation of 4-(4-fluorophenyl)pyridine

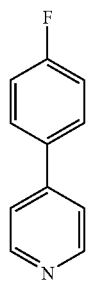

A mixture of 0.34 g (0.3 mmol) of tetrakis(triphenylphosphine)palladium, 1.94 g (10 mmol) of 4-bromopyridine hydrochloride, 19 mL of toluene, 15 mL of an aqueous sodium carbonate solution and 1.54 g (11 mmol) of 4-fluoroboronic acid is heated to 80° C. under argon for 5 hours.

The medium is taken up with ethyl acetate, washed with water, dried over magnesium sulfate, filtered and concentrated. The resultant residue is purified by silica gel chromatography (eluent: heptane/ethyl acetate 2/1).

Yield: 70% (white solid) $^1$H NMR (CDCl$_3$): 8.75 to 8.6 (unresolved peaks, 2H); 7.7 to 7.55 (unresolved peaks, 2H); 7.55 to 7.4 (unresolved peaks, 2H); 7.3 to 7.1 (unresolved peaks, 2H)

Step b: Preparation of 4-(4-fluorophenyl)pyridine-1-oxide

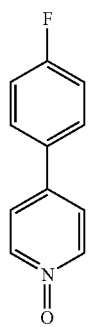

3.5 g (10.2 mmol) of meta-chloroperbenzoic acid are added to a solution of 1.18 g (6.81 mmol) of 4-(4-fluorophenyl)pyridine in 5 mL of chloroform cooled to 0° C. The suspension is stirred for 30 minutes.

The product is purified by chromatography on silica (eluent: ethyl acetate then dichloromethane/methanol 90/10).

Yield: 70% (white solid) $^1$H NMR (CDCl$_3$): 8.3 to 8.15 (unresolved peaks, 2H); 7.7 to 7.55 (unresolved peaks, 2H); 7.55 to 7.4 (unresolved peaks, 2H); 7.3 to 7.1 (unresolved peaks, 2H)

Step c: Preparation of 4-(4-fluorophenyl)-2-chloropyridine

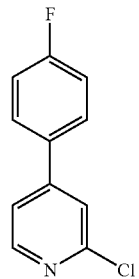

A mixture of 0.9 g (4.8 mmol) of 4-(4-fluorophenyl)pyridine-1-oxide and 10 mL of phosphoryl chloride is heated at reflux overnight.

After removing the excess phosphoryl chloride by vacuum distillation, the residue is taken up with 10 mL of toluene, after which it is again concentrated. The residue is solubilised in 25 mL of toluene, washed with 10 mL of water and with 10 mL of a saturated aqueous sodium hydrogencarbonate solution. The organic phase is dried over magnesium sulfate, filtered and concentrated. The resultant solid is taken up in heptane and is filtered under a vacuum.

Yield: 64% (white solid) $^1$H NMR (CDCl$_3$): 8.4 (doublet, 1H, J=5 Hz); 7.7 to 7.55 (unresolved peaks, 2H); 7.5 (singlet, 1H); 7.4 (doublet, 1H, J=5 Hz); 7.3 to 7.1 (unresolved peaks, 2H)

Step d: Preparation of 2-{4-[4-(3-trifluoromethylphenyl)piperazin-1-yl]butyl}amino-4-(4-fluorophenyl)pyridine

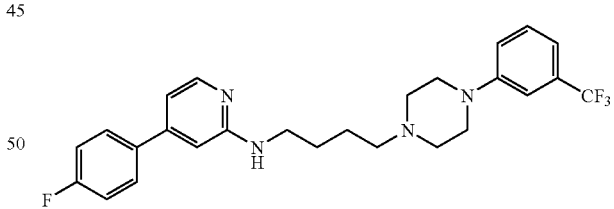

2-{4-[4-(3-Trifluoromethylphenyl)piperazin-1-yl]butyl}amino-4-(4-fluoro-phenyl)pyridine is then obtained from 4-(4-fluorophenyl)-2-chloropyridine using the same reaction sequence as that described in Example 14, steps a to c.

White solid Melting point: 85° C. $^1$H NMR (CDCl$_3$): 8.1 (doublet, 1H, J=5 Hz); 7.7 to 7.5 (unresolved peaks, 2H); 7.35 (triplet, 1H, J=7 Hz); 7.25 (unresolved peaks, 5H); 6.75 (doublet, 1H, J=5 Hz); 6.55 (singlet, 1H); 5.2 (wide singlet, 1H); 3.4 (multiplet, 2H); 3.3 (multiplet, 4H); 2.6 (multiplet, 4H); 2.55 (triplet, 2H, J=7 Hz); 2.05 to 1.65 (unresolved peaks, 4H)

Example 22

Preparation of 2-{4-[4-(3-trifluoromethylphenyl)piperazin-1-yl]butyl}-amino-4-(4-chlororophenyl)pyridine Step a: Preparation of 4-(4-chlorophenyl)pyridine

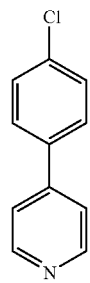

4-(4-Chlorophenyl)pyridine is obtained from 4-bromopyridine hydrochloride and 4-chlorophenylboronic acid using the same method as that described in Example 21, step a.

Yield: 90% (white solid) $^1$H NMR (CDCl$_3$): 8.75 to 8.6 (unresolved peaks, 2H); 7.6 to 7.5 (unresolved peaks, 2H); 7.55 to 7.4 (unresolved peaks, 4H)

Step b: Preparation of 4-(4-chlorophenyl)-2-chloropyridine

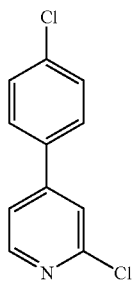

4-(4-Chlorophenyl)-2-chloropyridine is prepared from 4-(4-chlorophenyl)-pyridine using the same reaction sequence as that described for the preparation of 4-(4-fluorophenyl)-2-chloropyridine (Example 21, steps b and c).

$^1$H NMR (CDCl$_3$): 8.45 (doublet, 1H, J=5 Hz); 7.65 to 7.35 (unresolved peaks, 6H)

Step c: Preparation of 2-{4-[4-(3-trifluoromethylphenyl)piperazin-1-yl]butyl}-amino-4-(4-chlorophenyl)pyridine

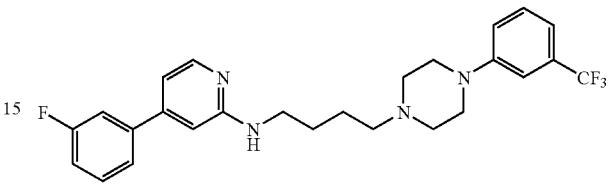

2-{4-[4-(3-Trifluoromethylphenyl)piperazin-1-yl]butyl}amino-4-(4-chloro-phenyl)pyridine is prepared from 4-(4-chlorophenyl)-2-chloropyridine using the same reaction sequence as that described for Example 14, steps a to c.

White solid $^1$H NMR (CDCl$_3$): 8.1 (doublet, 1H, J=5 Hz); 7.6 to 7.25 (unresolved peaks, 5H); 7.15 to 7.0 (unresolved peaks, 3H); 6.75 (multiplet, 1H); 6.5 (singlet, 1H); 5.0 (wide singlet, 1H); 3.4 (multiplet, 2H); 3.3 (multiplet, 4H); 2.6 (multiplet, 4H); 2.5 (triplet, 2H, J=7 Hz); 1.85 to 1.6 (unresolved peaks, 4H)

Example 23

Preparation of 2-{4-[4-(3-trifluoromethylphenyl)piperazin-1-yl]butyl}-amino-4-(3-fluorophenyl)pyridine

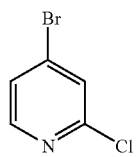

Step a: Preparation of 2-chloro-4-bromopyridine 81.5 mL of an aqueous solution of 48% strength hydrobromic acid are added, at 0° C., to 8.9 g (69.2 mmol) of 2-chloro-4-aminopyridine. 33.4 g (208.75 mmol) of molecular bromine are then added over a period of 10 minutes.

The solution is cooled to −10° C. and a solution of 10.65 g (154 mmol) of sodium nitrite in 20 mL of water is poured in over a period of 30 minutes. The solution is stirred for a further 10 minutes at −10° C., then for 1 h30 at ambient temperature.

The solution is cooled to 5° C. and a saturated aqueous sodium sulfite solution is added until the reaction medium loses colour. The reaction medium is basified with the assistance of a 35% strength aqueous sodium hydroxide solution. The aqueous basic phase is extracted twice with diethyl oxide. The organic phases are combined, dried over magnesium sulfate, filtered and concentrated. The resultant yellow oil (13 g) is chromatographed on silica gel (eluent: 1/9 ethyl acetate/heptane).

Yield: 52% (slightly coloured oil) $^1$H NMR (CDCl$_3$): 8.25 (doublet, 1H, J=5 Hz); 7.55 (singlet, 1H); 7.4 (doublet, 1H, J=5 Hz)

Step b: Preparation of 2-chloro-4-bromopyridine-1-oxide

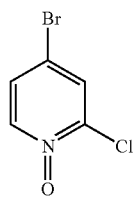

2-Chloro-4-bromopyridine-1-oxide is prepared from 2-chloro-4-bromopyridine using the same method as that described in Example 14, step a.

Yield: 46% (oil) $^1$H NMR (CDCl$_3$): 8.2 (doublet, 1H, J=7 Hz); 7.65 (singlet, 1H); 7.35 (multiplet, 1H)

Step c: Preparation of 2-{4-[4-(3-trifluoromethylphenyl)piperazin-1-yl]butyl}-amino-4-bromopyridine-1-oxide

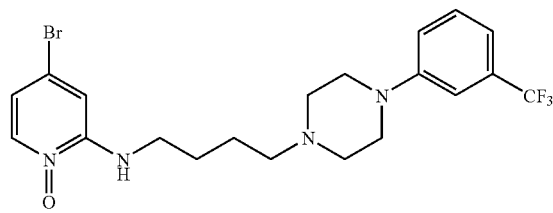

2-{4-[4-(3-Trifluoromethylphenyl)piperazin-1-yl]butyl}amino-4-bromo-pyridine-1-oxide is prepared from 2-chloro-4-bromopyridine-1-oxide and 4-[4-(3-trifluoromethyl)phenyl)piperazin-1-yl]butylamine (Example 3, step b) using the same method as that described in Example 14, step b.

Yield 72% (crystalline product)

$^1$H NMR (CDCl$_3$): 7.95 (doublet, 1H, J=7 Hz); 7.4 (triplet, 1H, J=7 Hz); 7.2 to 7.05 (unresolved peaks, 3H); 7.0 (wide triplet, 1H); 6.75 (singlet, 1H); 6.65 (doublet, 1H, J=7 Hz); 3.4 to 3.2 (unresolved peaks, 6H); 2.7 (unresolved peaks, 4H); 2.5 (triplet, 2H, J=7 Hz); 1.9 to 1.6 (unresolved peaks, 4H)

Step d: Preparation of 2-{4-[4-(3-trifluoromethylphenyl)piperazin-1-yl]butyl}-amino-4-(3-fluorophenyl)pyridine-1-oxide

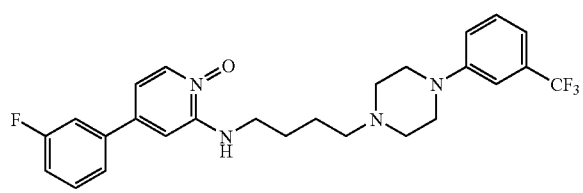

A mixture of 0.4 g (1 mmol) 2-{4-[4-(3-trifluoromethylphenyl)piperazin-1-yl]butyl}amino-4-bromopyridine-1-oxide, 3 mL of dioxane, 2.08 mL of a 2M aqueous sodium carbonate solution, 36 mg (0.3 mmol) of tetrakis(triphenylphosphine)palladium and 0.15 g (1.1 mmol) of 3-fluorophenylboronic acid is heated at reflux for 8 hours.

The reaction medium is diluted with ethyl acetate and washed twice with water. The organic phase is dried over magnesium sulfate, filtered and concentrated. The resultant oily residue (0.3 g) is chromatographed on silica gel (eluent: dichloromethane/methanol 95/5).

Yield: 38% (viscous oil) $^1$H NMR (CDCl$_3$): 8.15 (doublet, 1H, J=7 Hz); 7.5 to 7.2 (unresolved peaks, 4H); 7.2 to 7.0 (unresolved peaks, 4H); 6.9 (wide triplet, 1H); 6.85 to 6.65 (unresolved peaks, 2H); 3.4 (multiplet, 2H); 3.25 (multiplet, 4H); 2.6 (multiplet, 4H); 2.5 (triplet, 2H, J=7 Hz); 1.9 to 1.6 (unresolved peaks, 4H)

Step e: Preparation of 2-{4-[4-(3-trifluoromethylphenyl)piperazin-1-yl]butyl}-amino-4-(3-fluorophenyl)pyridine

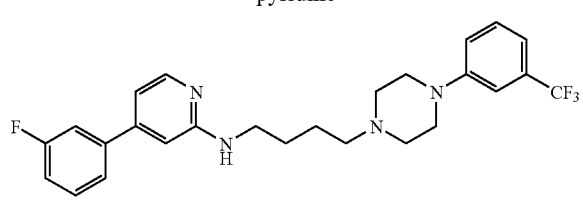

2-{4-[4-(3-Trifluoromethylphenyl)piperazin-1-yl]butyl}amino-4-(3-fluoro-phenyl)pyridine is obtained by reduction of 2-{4-[4-(3-trifluoro-methylphenyl)piperazin-1-yl]butyl}amino-4-(3-fluorophenyl)pyridine-1-oxide by phosphorus trichloride using the same method as that described in Example 14, step c.

White solid $^1$H NMR (CDCl$_3$): 8.1 (doublet, 1H, J=5 Hz); 7.55 to 7.2 (unresolved peaks, 4H); 7.2 to 7.0 (unresolved peaks, 4H); 6.8 (doublet, 1H, J=5 Hz); 6.6 (singlet, 1H); 5.25 (wide singlet, 1H); 3.5 to 3.2 (unresolved peaks, 6H); 2.7 (multiplet, 4H); 2.6 (wide triplet, 2H); 1.85 to 1.65 (unresolved peaks, 4H)

The products of Examples 24 to 38 are prepared using the same reaction sequence as that described for the preparation of Example 23.

Example 24

Preparation of 2-{4-[4-(3-trifluoromethylphenyl)piperazin-1-yl]butyl}-amino-4-(4-methoxyphenyl)pyridine

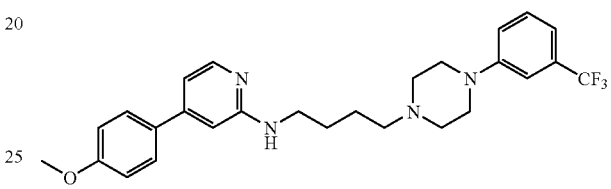

Very viscous oil $^1$H NMR (CDCl$_3$): 8.1 (wide singlet, 1H); 7.65 to 7.5 (unresolved peaks, 2H); 7.35 (triplet, 1H, J=7 Hz); 7.15 to 7.0 (unresolved peaks, 3H); 7.0 to 6.9 (unresolved peaks, 2H); 6.8 (doublet, 1H, J=5 Hz); 6.5 (singlet, 1H); 4.9 (wide singlet, 1H); 3.85 (singlet, 3H); 3.4 (multiplet, 2H); 3.3 (multiplet, 4H); 2.6 (multiplet, 4H); 2.45 (triplet, 2H, J=7 Hz); 1.85 to 1.6 (unresolved peaks, 4H)

Example 25

Preparation of 2-{4-[4-(3-trifluoromethylphenyl)piperazin-1-yl]butyl}-amino-4-(3-thienyl)pyridine

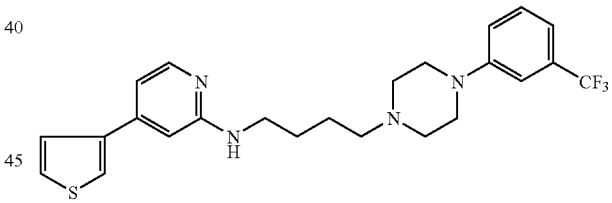

White crystalline solid Melting point: 95° C. $^1$H NMR (CDCl$_3$): 8.05 (doublet, 1H, J=5 Hz); 7.6 (singlet, 1H); 7.5 to 7.25 (unresolved peaks, 3H); 7.2 to 7.0 (unresolved peaks, 3H); 6.8 (doublet, 1H, J=5 Hz); 6.55 (singlet, 1H); 4.9 (wide singlet, 1H); 3.35 (multiplet, 2H); 3.25 (multiplet, 4H); 2.6 (multiplet, 4H); 2.5 (triplet, 2H, J=7 Hz): 1.85 to 1.6 (unresolved peaks, 4H)

Example 26

Preparation of 2-{4-[4-(3-trifluoromethylphenyl)piperazin-1-yl]butyl}-amino-4-(2-furyl)pyridine

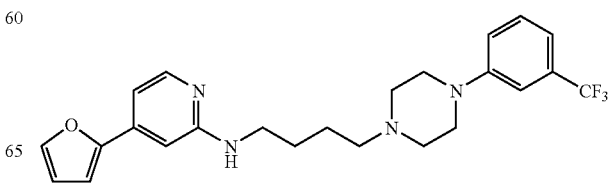

White crystalline solid Melting point: 98° C. $^1$H NMR (CDCl$_3$): 8.05 (doublet, 1H, J=5 Hz); 7.5 (singlet, 1H); 7.35 (triplet, 1H, J=7 Hz); 7.2 to 7.0 (unresolved peaks, 3H); 6.9 to 6.7 (unresolved peaks, 2H); 6.65 (singlet, 1H); 6.5 (multiplet, 1H); 4.85 (wide singlet, 1H); 3.4 (multiplet, 2H); 3.25 (multiplet, 4H); 2.6 (multiplet, 4H); 2.45 (triplet, 2H, J=7 Hz); 1.85 to 1.55 (unresolved peaks, 4H)

Example 27

Preparation of 2-{4-[4-(3-trifluoromethylphenyl)piperazin-1-yl]butyl}-amino-4-(2-thienyl)pyridine

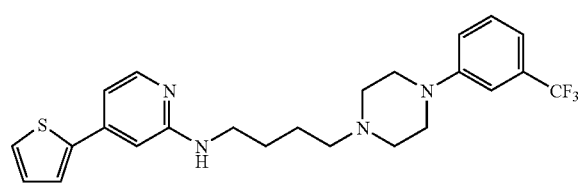

White crystalline solid Melting point: 95° C. $^1$H NMR (CDCl$_3$): 8.05 (doublet, 1H, J=5 Hz); 7.5 to 7.25 (unresolved peaks, 3H); 7.2 (unresolved peaks, 4H); 6.8 (doublet, 1H, J=5 Hz); 6.5 (singlet, 1H); 5.0 (wide singlet, 1H); 3.35 (multiplet, 2H); 3.25 (multiplet, 4H); 2.65 (multiplet, 4H); 2.5 (triplet, 2H, J=7 Hz); 1.85 to 1.6 (unresolved peaks, 4H)

Example 28

Preparation of 2-{4-[4-(3-trifluoromethylphenyl)piperazin-1-yl]butyl}-amino-4-(2-fluorophenyl)pyridine

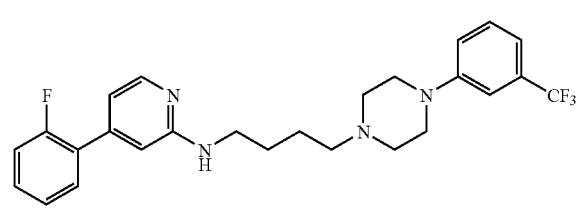

White crystalline solid Melting point: 100° C. $^1$H NMR (CDCl$_3$): 8.15 (doublet, 1H, J=7 Hz); 7.5 to 7.0 (unresolved peaks, 8H); 6.75 (doublet, 1H, J=5.5 Hz); 6.56 (singlet, 1H); 4.8 (wide triplet, 1H); 3.35 (multiplet, 2H); 3.25 (multiplet, 4H); 2.6 (multiplet, 4H); 2.45 (triplet, 2H, J=7 Hz); 1.85 to 1.6 (unresolved peaks, 4H)

Example 29

Preparation of 2-{4-[4-(3-trifluoromethylphenyl)piperazin-1-yl]butyl}-amino[4,4']bipyridine

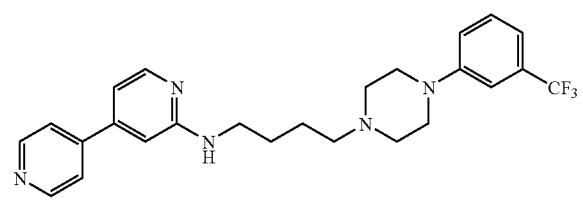

Viscous oil $^1$H NMR (CDCl$_3$): 8.65 (doublet, 1H, J=5 Hz); 8.1 (doublet, 1H, J=5 Hz); 7.5 to 7.2 (unresolved peaks, 4H); 7.2 to 7.0 (unresolved peaks, 3H); 6.8 (multiplet, 1H); 6.55 (singlet, 1H); 5.5 (wide singlet, 1H); 3.4 (multiplet, 2H); 3.2 (unresolved peaks, 4H); 2.65 (multiplet, 4H); 2.5 (triplet, 2H, J=7 Hz); 1.85 to 1.5 (unresolved peaks, 4H)

Example 30

Preparation of 2-{4-[4-(3-trifluoromethylphenyl)piperazin-1-yl]butyl}-amino-4-(3-methylphenyl)pyridine

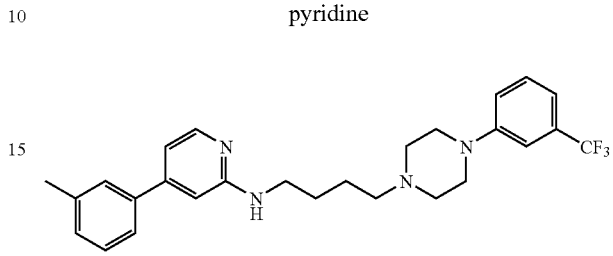

White crystalline solid Melting point: 87° C. $^1$H NMR (CDCl$_3$): 8.05 (doublet, 1H, J=5 Hz); 7.5 to 7.15 (unresolved peaks, 5H); 7.2 to 7.0 (unresolved peaks, 3H); 6.8 (multiplet, 1H); 6.6 (singlet, 1H); 4.4 (wide singlet, 1H); 3.4 (multiplet, 2H); 3.3 (multiplet, 4H); 2.65 (multiplet, 4H); 2.5 (triplet, 2H, J=7 Hz); 2.4 (singlet, 3H); 1.85 to 1.55 (unresolved peaks, 4H)

Example 31

Preparation of 2-{4-[4-(3-trifluoromethylphenyl)piperazin-1-yl]butyl}-amino-4-(3-methoxyphenyl)pyridine

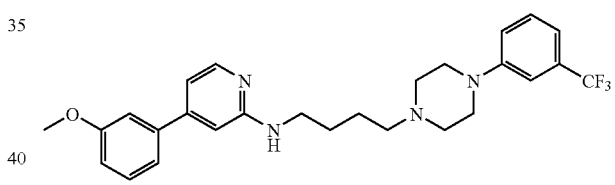

White solid Melting point: 73° C. $^1$H NMR (CDCl$_3$): 8.1 (doublet, 1H, J=5 Hz); 7.45 to 7.25 (unresolved peaks, 2H); 7.2 to 7.0 (unresolved peaks, 5H); 6.95 (doublet, 1H, J=5 Hz); 6.8 (multiplet, 1H); 6.55 (singlet, 1H); 5.05 (wide singlet, 1H); 3.85 (singlet, 3H); 3.4 (multiplet, 2H); 3.3 (multiplet, 4H); 2.65 (multiplet, 4H); 2.45 (triplet, 2H, J=7 Hz); 1.85 to 1.65 (unresolved peaks, 4H)

Example 32

Preparation of 2-{4-[4-(3-trifluoromethylphenyl)piperazin-1-yl]butyl}-amino[4,3']bipyridine

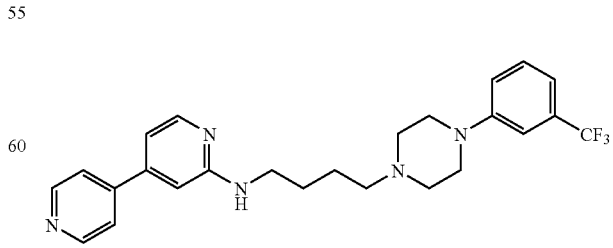

White crystalline solid Melting point: 112° C. $^1$H NMR (CDCl$_3$): 8.85 (singlet, 1H); 8.65 (doublet, 1H, J=5 Hz); 8.15

(doublet, 1H, J=5 Hz); 7.9 (multiplet, 1H); 7.45 to 7.25 (unresolved peaks, 2H); 7.2 to 7.0 (unresolved peaks, 3H); 6.8 (multiplet, 1H); 6.55 (singlet, 1H); 5.0 (wide singlet, 1H); 3.4 (multiplet, 2H); 3.3 (multiplet, 4H); 2.65 (multiplet, 4H); 2.5 (triplet, 2H, J=7 Hz); 1.85 to 1.6 (unresolved peaks, 4H)

Example 33

Preparation of 2-{4-[4-(3-trifluoromethylphenyl)piperazin-1-yl]butyl}-amino-4-(4-trifluoromethoxyphenyl)pyridine

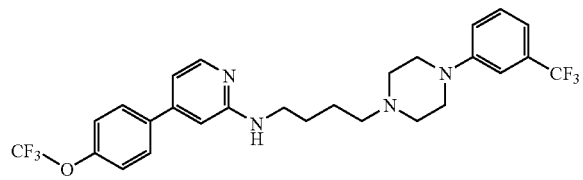

White crystalline solid Melting point: 72° C. $^1$H NMR (CDCl$_3$): 8.1 (doublet, 1H, J=5 Hz); 7.65 to 7.5 (unresolved peaks, 2H); 7.45 to 7.2 (unresolved peaks, 3H); 7.15 to 7.0 (unresolved peaks, 3H); 6.75 (multiplet, 1H); 6.5 (singlet, 1H); 5.0 (wide singlet, 1H); 3.35 (multiplet, 2H); 3.2 (multiplet, 4H); 2.65 (multiplet, 4H); 2.5 (triplet, 2H, J=7 Hz); 1.85 to 1.55 (unresolved peaks, 4H)

Example 34

Preparation of 2-{4-[4-(3-trifluoromethylphenyl)piperazin-1-yl]butyl}-amino-4-(4-acetylphenyl)pyridine

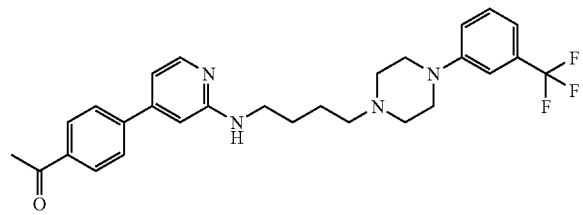

Viscous oil $^1$H NMR (CDCl$_3$): 8.15 (doublet, 1H, J=5 Hz); 8.1 to 7.95 (unresolved peaks, 2H); 7.75 to 7.6 (unresolved peaks, 2H); 7.35 (triplet, 1H, J=7.5 Hz); 7.2 to 7.0 (unresolved peaks, 3H); 6.8 (doublet, 1H, J=5 Hz); 6.6 (singlet, 1H); 5.0 (wide triplet, 1H); 3.4 (multiplet, 2H); 3.3 (multiplet, 4H); 2.7 to 2.55 (unresolved peaks, 7H); 2.5 (multiplet, 2H); 1.85 to 1.6 (unresolved peaks, 4H)

Example 35

Preparation of 2-{4-[4-(3-trifluoromethylphenyl)piperazin-1-yl]butyl}-amino-4-(3-acetylphenyl)pyridine

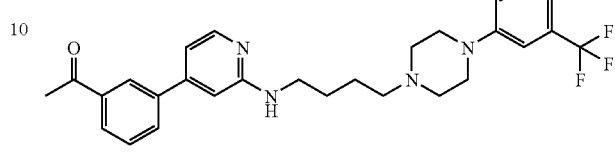

Viscous oil $^1$H NMR (CDCl$_3$): 8.25 to 8.05 (unresolved peaks, 2H); 8.0 (doublet, 1H, J=7 Hz); 7.8 (doublet, 1H, J=7 Hz); 7.55 (triplet, 1H, J=7 Hz); 7.35 (triplet, 1H, J=7 Hz); 7.2 to 7.0 (unresolved peaks, 3H); 6.8 (singlet, 1H); 6.65 (singlet, 1H); 5.2 (triplet, wide, 1H); 3.4 (multiplet, 2H); 3.3 (multiplet, 4H); 2.7 (multiplet, 4H); 2.65 (singlet, 3H); 2.55 (multiplet, 2H); 1.85 to 1.6 (unresolved peaks, 4H)

Example 36

Preparation of 2-{4-[4-(3-trifluoromethylphenyl)piperazin-1-yl]butyl}-amino-4-(4-hydroxymethylphenyl)pyridine

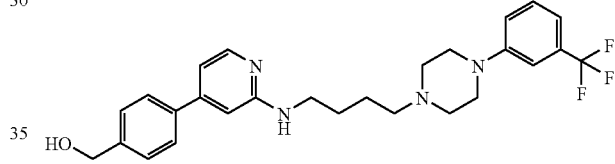

Viscous oil $^1$H NMR (CDCl$_3$): 8.1 (doublet, 1H, J=5 Hz); 7.65 to 7.5 (unresolved peaks, 2H); 7.5 to 7.4 (unresolved peaks, 2H); 7.35 (triplet, 1H, J=7.5 Hz); 7.15 to 7.0 (unresolved peaks, 3H); 7.75 (doublet, 1H, J=5 Hz); 6.5 (singlet, 1H); 5.0 (triplet, wide, 1H); 4.7 (singlet, 2H); 3.4 (multiplet, 2H); 3.25 (multiplet, 4H); 2.8 (wide singlet, 1H); 2.6 (multiplet, 4H); 2.45 (multiplet, 2H); 1.85 to 1.55 (unresolved peaks, 4H)

Example 37

Preparation of 2-{4-[4-(3-trifluoromethylphenyl)piperazin-1-yl]butyl}-amino-4-(benzo[1,3]dioxol-5-yl)pyridine

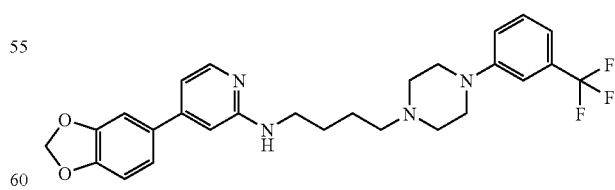

Amorphous white solid $^1$H NMR (CDCl$_3$): 8.1 (doublet, 1H, J=5 Hz); 7.35 (triplet, 1H, J=7.5 Hz); 7.2 to 7.0 (unresolved peaks, 5H); 6.9 (doublet, 1H, J=7.5 Hz); 6.75 (multiplet, 1H); 6.5 (singlet, 1H); 6.0 (singlet, 2H); 4.8 (triplet, wide, 1H); 3.35 (multiplet, 2H); 3.3 (multiplet, 4H); 2.6 (multiplet, 4H); 2.5 (multiplet, 2H); 1.8 to 1.55 (unresolved peaks, 4H)

Example 38

Preparation of 2-{4-[4-(3-trifluoromethylphenyl)piperazin-1-yl]butyl}-amino-4-(4-ethoxycarbonylphenyl)pyridine

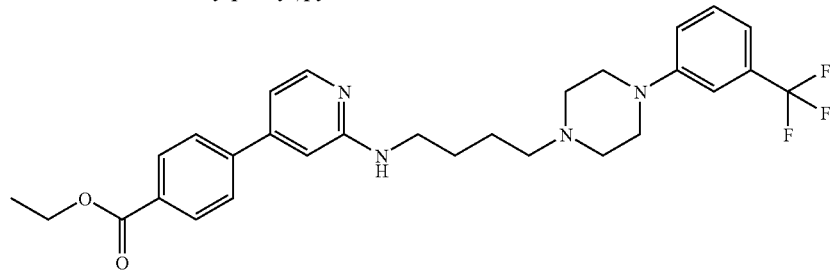

Yellow solid Melting point: 101° C. $^1$H NMR (CDCl$_3$): 8.25 to 8.0 (unresolved peaks, 3H); 7.8 to 7.55 (unresolved peaks, 2H); 7.35 (triplet, 1H, J=7.5 Hz); 7.2 to 7.0 (unresolved peaks, 3H); 6.8 (doublet, 1H, J=5 Hz); 6.6 (singlet, 1H); 5.15 (triplet, wide, 1H); 4.4 (quadruplet, 2H, J=7.5 Hz); 3.4 (multiplet, 2H); 3.3 (multiplet, 4H); 2.7 (multiplet, 4H); 2.55 (multiplet, 2H); 1.9 to 1.65 (unresolved peaks, 4H); 1.4 (triplet, 3H, J=7.5 Hz)

Example 39

Preparation of 2-{4-[4-(3-trifluoromethylphenyl)piperazin-1-yl]butyl}-amino-4-(4-(1-hydroxyethyl)phenyl)pyridine

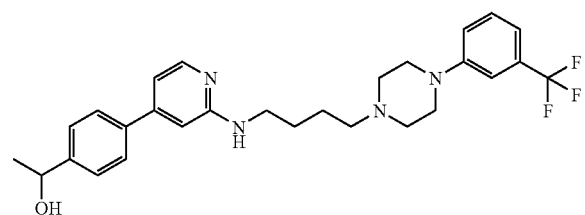

10 mg (2.6 mmol) of sodium borohydride are added at 5° C. to a solution of 50 mg (0.1 mmol) of 2-{4-[4-(3-trifluoromethyl-phenyl)piperazin-1-yl]butyl}amino-4-(4-acetylphenyl)pyridine (Example 34) in 5 mL of methanol. The solution is stirred for 2 hours at ambient temperature.

After addition of 20 mL of water, the product is extracted twice with 20 mL of ethyl acetate. The organic phase is washed with water, dried over magnesium sulfate, filtered and concentrated. The oily residue is purified by silica gel chromatography (eluent: 95/5 dichloromethane/methanol).

Viscous oil $^1$H NMR (CDCl$_3$): 8.1 (doublet, 1H, J=5 Hz); 7.65 to 7.5 (unresolved peaks, 2H); 7.5 to 7.4 (unresolved peaks, 2H); 7.3 (triplet, 1H, J=7.5 Hz); 7.2 to 7.0 (unresolved peaks, 3H); 6.8 (multiplet, 1H); 6.5 (singlet, 1H); 5.0 (triplet, wide, 1H); 4.95 (quadruplet, 1H, J=7 Hz); 3.35 (multiplet, 2H); 3.3 (multiplet, 4H); 2.6 (multiplet, 4H); 2.45 (multiplet, 2H); 2.4 (wide singlet, 1H); 1.85 to 1.6 (unresolved peaks, 4H); 1.5 (doublet, 3H, J=7 Hz)

Example 40

Preparation of 2-{4-[4-(3-trifluoromethylphenyl)piperazin-1-yl]butyl}-amino-4-(4-(1-hydroxy-1-methylethyl)phenyl)pyridine

2 mL of a 2.6 M methylmagnesium chloride solution in tetrahydrofuran are added under argon and at 0° C. to a solution of 0.1 g (0.2 mmol) of 2-{4-[4-(3-trifluoromethyl-phenyl)piperazin-1-yl]butyl}amino-4-(4-acetylphenyl)pyridine (Example 34) in 2 mL of anhydrous tetrahydrofuran. The temperature is maintained at 0° C. for 30 minutes.

After returning to ambient temperature, the solution is diluted with ethyl acetate, washed with water, dried over magnesium sulfate, filtered and concentrated. The residual oil is purified by silica gel chromatography (eluent: dichloromethane/methanol 96/4).

Viscous oil $^1$H NMR (CDCl$_3$): 8.1 (doublet, 1H, J=5 Hz); 7.55 (singlet, 4H); 7.35 (triplet, 1H, J=7.5 Hz); 7.15 to 7.0 (unresolved peaks, 3H); 6.8 (multiplet, 1H); 6.55 (singlet, 1H); 5.1 (wide triplet, 1H); 3.35 (multiplet, 2H); 3.25 (multiplet, 4H); 2.65 (multiplet, 4H); 2.5 (multiplet, 2H); 2.0 (singlet, wide, 1H); 1.85 to 1.65 (unresolved peaks, 4H); 1.6 (singlet, 6H)

Example 41

Preparation of 2-{4-[4-(3-trifluoromethylphenyl)piperazin-1-yl]butyl}-amino-4-(3-(1-hydroxy-1-methylethyl)phenyl)pyridine

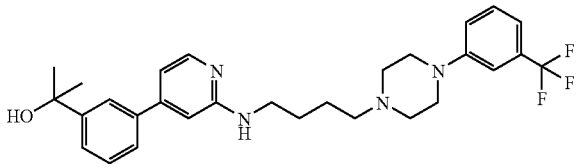

2-{4-[4-(3-Trifluoromethylphenyl)piperazin-1-yl]butyl}amino-4-(3-(1-hydroxy-1-methylethyl)phenyl)pyridine is prepared from 2-{4-[4-(3-trifluoromethylphenyl)piperazin-1-yl]butyl}amino-4-(3-acetylphenyl)pyridine (Example 35) using the same method as that used in Example 40.

Viscous oil $^1$H NMR (CDCl$_3$): 8.1 (doublet, 1H, J=5 Hz); 7.75 (singlet, 1H); 7.6 to 7.4 (unresolved peaks, 3H); 7.35 (triplet, 1H, J=7.5 Hz); 7.2 to 7.0 (unresolved peaks, 3H); 6.8 (doublet, 1H, J=5 Hz); 6.6 (singlet, 1H); 5.15 (wide triplet, 1H); 3.4 (multiplet, 2H); 3.3 (multiplet, 4H); 2.65 (multiplet, 4H); 2.5 (multiplet, 2H); 2.2 (wide singlet, 1H); 1.85 to 1.7 (unresolved peaks, 4H); 1.65 (singlet, 6H)

Example 42

Preparation of 2-{4-[4-(3-trifluoromethylphenyl)piperazin-1-yl]butyl}-amino-4-(4-carboxyphenyl)pyridine sodium salt

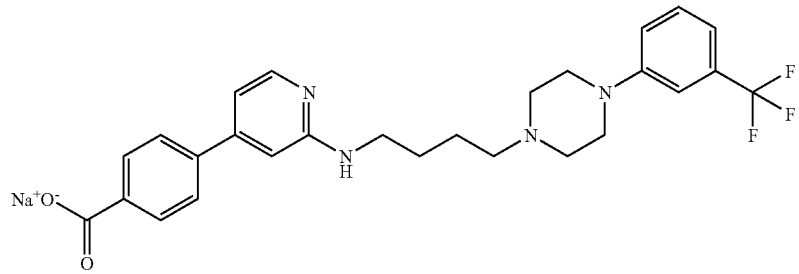

A mixture of 80 mg (1.5 mmol) of 2-{4-[4-(3-trifluoromethyl-phenyl)piperazin-1-yl]butyl}amino-4-(4-ethoxycarbonylphenyl)pyridine (Example 38), 10 mL of ethanol and 1.5 mL of a 0.1 N aqueous sodium hydroxide solution is heated at reflux for 4 hours.

The solution is concentrated under a vacuum. The residual solid is comminuted in diethyl oxide, filtered and dried under a vacuum.

Solid $^1$H NMR (methanol D$_4$): 8.1 to 7.85 (unresolved peaks, 3H); 7.6 to 7.5 (unresolved peaks, 2H); 7.35 (triplet, 1H, J=7.5 Hz); 7.2 to 6.9 (unresolved peaks, 3H); 6.9 to 6.65 (unresolved peaks, 2H); 3.5 to 3.1 (unresolved peaks, 6H); 2.6 (multiplet, 4H); 2.5 (multiplet, 2H); 1.8 to 1.5 (unresolved peaks, 4H)

Example 43

Preparation of 2-{4-[4-(3-trifluoromethylphenyl)piperazin-1-yl]butyl}-amino-4-phenylthiazole

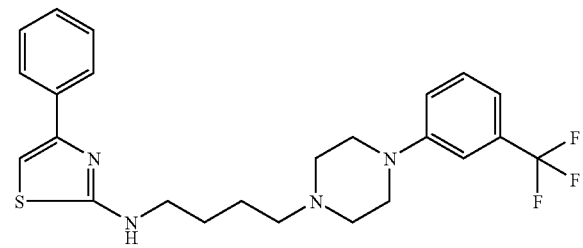

A mixture of 0.19 g (1 mmol) of 2-chloro-4-phenylthiazole (*Bull. Soc. Chim. Fr.*, 2498, 1963) and 0.3 g (1 mmol) of 4-[4-(3-trifluoromethyl-phenyl)piperazine-1-yl]butylamine (Example 3, step b) is heated to 150° C. for 2 minutes.

The mixture is diluted with ethyl acetate, washed with a 0.5 N aqueous sodium hydroxide solution and then with water. The organic phase is dried over magnesium sulfate, filtered and concentrated. The resultant oily residue is purified by silica gel chromatography (eluent: dichloromethane/methanol 95/5).

Crystalline yellow solid: 155° C. Yield: 7% $^1$H NMR (CDCl$_3$): 7.8 (multiplet, 2H); 7.45 to 7.2 (unresolved peaks, 4H); 7.2 to 7.0 (unresolved peaks, 3H); 6.7 (singlet, 1H); 6.4 (wide triplet, 1H); 3.45 to 3.3 (unresolved peaks, 6H); 2.7 (multiplet, 4H); 2.5 (triplet, 2H, J=7 Hz); 1.9 to 1.6 (unresolved peaks, 4H)

Example 44

Preparation of 2-{4-[4-(3-trifluoromethylphenyl)piperazin-1-yl]butyl}-amino-5-phenyloxazole

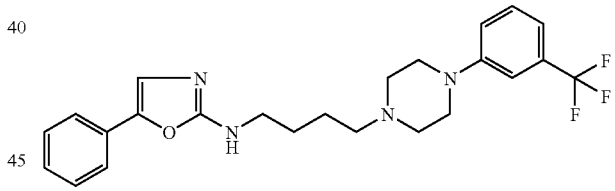

Step a: Preparation of 2-chloro-5-phenyloxazole

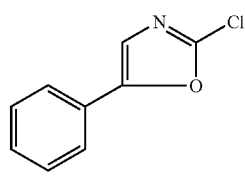

0.29 g (2.8 mmol) of triethylamine is added to a mixture of 0.5 g (2.8 mmol) of 5-phenyl-3H-oxazole-2-thione (FR 1,450,443) and 2.3 mL of phosphoryl chloride cooled to 0° C. The mixture is heated to 120° C. for 3 hours.

The medium is diluted with ethyl acetate and washed with water. The organic phase is dried over magnesium sulfate, filtered and concentrated. The product is purified by silica gel chromatography (eluent: 15/85 ethyl acetate/heptane).

Chestnut brown viscous oil
Yield: 18%

¹H NMR (CDCl₃): 7.7 to 7.55 (unresolved peaks, 2H); 7.5 to 7.3 (unresolved peaks, 3H); 7.25 (singlet, 1H)

Step b: Preparation of 2-{4-[4-(3-trifluoromethylphenyl)piperazin-1-yl]butyl}-amino-5-phenyloxazole

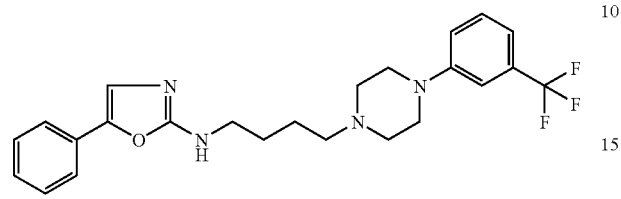

A solution of 35 mg (0.2 mmol) of 2-chloro-5-phenyloxazole in 0.5 mL of tetrahydrofuran is added, at 0° C., to a solution of 62 mg (0.2 mmol) of 4-[4-(3-trifluoromethylphenyl)piperazine-1-yl]butylamine (Example 3, step b) and 20 mg (0.2 mmol) of triethylamine in 0.2 mL of tetrahydrofuran. The mixture is stirred overnight under argon.

After concentration under a vacuum, the product is purified by silica gel chromatography (eluent: dichloromethane/methanol 97/3).

White solid Yield: 12% Melting point: 151° C. ¹H NMR (CDCl₃): 7.45 to 7.3 (unresolved peaks, 4H); 7.2 to 7.05 (unresolved peaks, 5H); 7.0 (singlet, 1H); 6.25 (wide singlet, 1H); 3.5 to 3.3 (unresolved peaks, 6H); 2.75 (multiplet, 4H); 2.55 (wide triplet, 2H); 1.9 to 1.7 (unresolved peaks, 4H)

Example 45

Preparation of 2-{4-[4-(3-trifluoromethyl-phenyl)piperazin-1-yl]butyl}-aminoquinoline

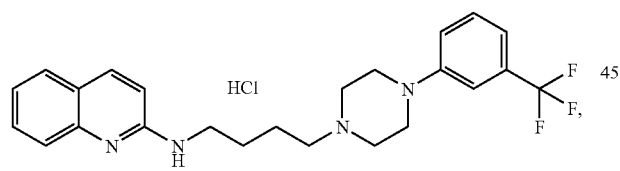

A mixture of 0.2 g (0.66 mmol) of 4-[4-(3-trifluoro-methylphenyl)piperazin-1-yl]butylamine (Example 3, step b) and 0.5 g (3.06 mmol) of commercial 2-chloroquinoline is heated at reflux for one minute. The reaction medium is then diluted with 15 mL of ethyl acetate and then washed with 10 mL of water. The organic phase is dried over magnesium sulfate, filtered and concentrated. The oily residue is chromatographed on silica gel (elution with ethyl acetate). After concentration of the elution fractions, 0.15 g of 2-{4-[4-(3-trifluoromethylphenyl)piperazine-1-yl]butyl}amino-quinoline is obtained.

Salification is performed by dissolution in 10 mL of diethyl oxide and addition of 1.5 mL of a saturated hydrogen chloride solution in diethyl oxide. After stirring for 5 minutes, the precipitate is filtered, washed with 5 mL of diethyl oxide and dried under a vacuum.

Mass obtained: 0.16 g (52%), white solid. Melting point: 170° C. (tube) ¹H NMR (D₂O): 8.25 to 8.0 (unresolved peaks, 1H); 7.85 to 7.6 (unresolved peaks, 3H); 7.55 to 7.35 (unresolved peaks, 2H); 7.35 to 7.15 (unresolved peaks, 3H); 7.05 to 6.85 (unresolved peaks, 1H); 3.9 (multiplet, 2H); 3.7 (multiplet, 2H); 3.55 (triplet, 2H); 3.35 to 3.05 (unresolved peaks, 6H); 2.0 to 1.7 (unresolved peaks, 4H)

Example 46

Preparation of 1-{4-[4-(3-trifluoromethylphenyl)piperazin-1-yl]butyl}-aminoisoquinoline hydrochloride

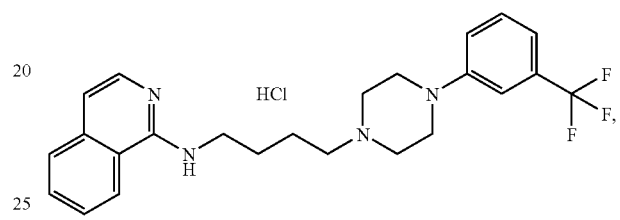

1-{4-[4-(3-Trifluoromethylphenyl)piperazin-1-yl]butyl}-aminoisoquinoline hydrochloride may be obtained from commercial 1-chloroisoquinoline and 4-[4-(3-trifluoromethylphenyl)piperazin-1-yl]butylamine (Example 3, step b) using the same method as that described in Example 14.

Yield: 33%, pinkish solid. Melting point: 260° C. (tube) ¹H NMR (D₂O): 8.25 (doublet, 1H); 8.0 to 7.8 (unresolved peaks, 2H); 7.7 (triplet, 1H); 7.55 to 7.3 (unresolved peaks, 2H); 7.3 to 7.2 (unresolved peaks, 3H); 7.15 (doublet, 1H); 3.9 (multiplet, 2H); 3.7 (multiplet, 2H); 3.6 (triplet, 2H); 3.35 to 3.0 (unresolved peaks, 6H); 2.0 to 1.7 (unresolved peaks, 4H)

Example 47

Preparation of 2-{4-[4-(2,3-dichlorophenyl)-piperazin-1-yl]butyl}-aminoquinoline hydrochloride

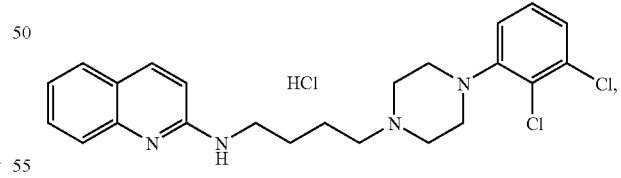

2-{4-[4-(2,3-Dichlorophenyl)piperazin-1-yl]butyl}amino-quinoline hydrochloride may be obtained from 2-chloroquinoline and 4-[4-(2,3-dichlorophenyl)piperazin-1-yl]butylamine (Example 6, step b) using the same method as that described in Example 45.

Yield: 38%, white solid. Melting point: 280° C. (tube) ¹H NMR (D₂O): 8.2 (doublet, 1H); 7.75 to 7.6 (unresolved peaks, 2H); 7.55 (multiplet, 1H); 7.4 to 7.25 (unresolved peaks, 3H); 7.15 (doublet, 1H); 7,0 (doublet, 1H); 3.9 to 2.9 (multiplet, 12H); 2.0 to 1.7 (unresolved peaks, 4H)

Example 48

Preparation of 1-{4-[4-(2,3-dichlorophenyl)-piperazin-1-yl]butyl}-aminoisoquinoline hydrochloride

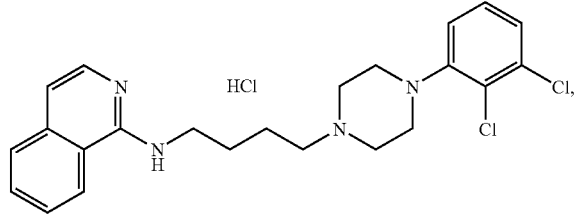

1-{4-[4-(2,3-Dichlorophenyl)piperazin-1-yl]butyl}amino-isoquinoline hydrochloride may be obtained from 1-chloroisoquinoline and 4-[4-(2,3-dichlorophenyl)piperazin-1-yl]butylamine (Example 6, step b) using the same method as that described in Example 45.

Yield: 44%, white solid. Melting point: 150° C. (tube) $^1$H NMR (D$_2$O): 8.25 (doublet, 1H); 8 to 7.8 (unresolved peaks, 2H); 7.7 (triplet, 1H); 7.55 (doublet, 1H); 7.4 to 7.2 (unresolved peaks, 2H); 7.2 to 7.05 (unresolved peaks, 2H); 3.9 to 2.9 (multiplet, 12H); 2.05 to 1.75 (unresolved peaks, 4H)

Example 49

Determination of the Affinity of the Compounds for the Human D3 Dopamine and Human alpha-1 Adrenergic Receptors

[$^3$H] Spiperone Binding

CHO cells were transfected with the gene coding for the human D3 dopamine receptor (hD3). [$^3$H]spiperone binding (0.5 to 2 nM) is performed in the presence of 5 to 10 μg of membrane proteins in a medium containing 120 mM of NaCl, 5 mM of KCl, and 50 mM of Tris-HCl pH 7.4; incubation of 60 minutes at ambient temperature is necessary. Non-specific binding is estimated in the presence of 5 μM of haloperidol. Non-transfected cells have absolutely no binding activity.

[$^3$H] Prasozin Binding

HEK 293 cells were transfected with the gene coding for the human alpha-1 adrenergic receptor (hα1). [3H]prasozin binding (0.02 to 2 nM) is performed in the presence of 5 to 10 μg of membrane proteins in a medium containing 0.5 mM of EDTA and 50 mM of Tris-HCl pH 7.4; incubation of 60 minutes at ambient temperature is necessary. Non-specific binding is estimated in the presence of 10 μM of phentolamine. Non-transfected cells have absolutely no binding activity.

TABLE 1

Antagonistic effects (Ki, nM) on the hD3 and hα1 receptors respectively measured by [$^3$H] spiperone and [$^3$H] prasozin binding.

| Example no. | hD3 Ki (nM) | hα1 Ki (nM) |
|---|---|---|
| 4 | 0.76 | 162.5 |
| 6 | 0.55 | 135.7 |

The invention claimed is:

1. A compound of the formula (I):

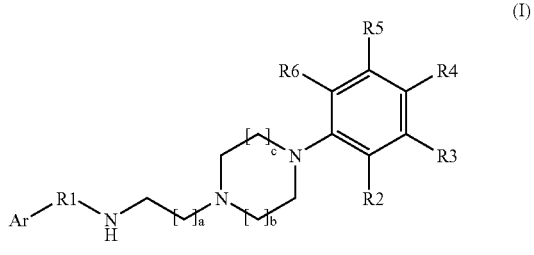

in which:
R1 represents a 2-pyridyl;
Ar is an aryl or heteroaryl, optionally substituted by one or more identical or different substituents selected from among a halogen atom or a hydroxy, alkyl, monofluoroalkyl, polyfluoroalkyl, alkoxy, polyfluoroalkoxy, alkylsulfanyl, polyfluoroalkylsulfanyl, cyano, carbamoyl, dialkylcarbamoyl, alkyl-C(=O)—, alkyl-O—C(=O)-, HO—C(=O)—(HO)alkyl group;
a=3;
b and c=1;
R2, R3, R4, R5 and R6 each independently represent a hydrogen or halogen atom or a hydroxy, alkyl, monofluoroalkyl, polyfluoroalkyl, alkoxy, polyfluoroalkoxy, alkylsulfanyl, polyfluoroalkylsulfanyl, cyano, —NRR', —COOR, —COR, —CONRR' group;
where R, R', identical or different, independently represent a hydrogen atom, or an alkyl group;
or the stereoisomer thereof, the tautomeric form thereof, or the pharmaceutically acceptable salt thereof.

2. A compound according to claim 1 such that Ar is an aryl, optionally substituted by one or more identical or different substituents selected from among a halogen atom or an alkyl group.

3. A compound according to claim 1 selected from the group consisting of:
2-{4-[4-(3-trifluoromethylphenyl)piperazin-1-yl]butyl}amino-4-phenylpyridine
2-{4-[4-(3-trifluoromethylphenyl)piperazin-1-yl]butyl}amino-4-phenylpyridine dihydrochloride
2-{4-[4-(2,3-dichlorophenyl)piperazin-1-yl]butyl}amino-4-phenylpyridine, or the stereoisomer thereof, the tautomeric form thereof, or the pharmaceutically acceptable salt thereof.

4. A pharmaceutical composition comprising a therapeutically effective quantity of at least one compound according to claim 1 in the form of a pharmaceutically acceptable salt or free form with a pharmaceutically acceptable vehicle or excipient.

* * * * *